United States Patent [19]

Kobayashi et al.

[11] Patent Number: 4,628,024
[45] Date of Patent: Dec. 9, 1986

[54] SILVER HALIDE COLOR PHOTOGRAPHIC LIGHT-SENSITIVE MATERIAL

[75] Inventors: Hidetoshi Kobayashi; Keiji Mihayashi; Isamu Itoh, all of Kanagawa, Japan

[73] Assignee: Fuji Photo Film Co., Ltd., Japan

[21] Appl. No.: 817,239

[22] Filed: Jan. 9, 1986

Related U.S. Application Data

[63] Continuation of Ser. No. 583,901, Feb. 27, 1984, abandoned.

[30] Foreign Application Priority Data

Feb. 25, 1983 [JP] Japan .................................. 58-31611

[51] Int. Cl.⁴ ................................................ G03C 1/40
[52] U.S. Cl. ..................... 430/376; 430/505; 430/543; 430/383; 430/955; 430/553; 430/555; 430/557; 430/558
[58] Field of Search .............. 430/955, 956, 957, 958, 430/505, 543, 544, 222, 223, 224, 225, 226, 376, 383, 553, 555, 557, 558

[56] References Cited

U.S. PATENT DOCUMENTS 4,390,618 6/1983 Kobayashi et al. .................. 430/955

*Primary Examiner*—Won H. Louie
*Attorney, Agent, or Firm*—Sughrue, Mion, Zinn, Macpeak and Seas

[57] ABSTRACT

A silver halide color photographic light-sensitive material comprising a support having thereon a silver halide emulsion layer and a compound represented by the following general formula (I):

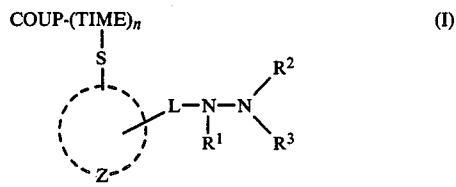

wherein COUP represents a coupler residue capable of being subjected to a coupling reaction with an oxidation product of an aromatic primary amine developing agent; TIME represents a timing group which is released upon the coupling reaction and subsequently releases

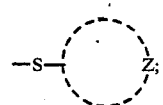

Z represents a monocyclic or condensed heterocyclic ring consisting of a nitrogen atom and a carbon atom; L represents a divalent linking group; $R^1$ represents a hydrogen atom or an alkoxycarbonyl group; $R^2$ represents a hydrogen atom, an alkyl group, an aryl group, a heterocyclic group, an acyl group, a sulfonyl group, an alkoxycarbonyl group, a carbamoyl group, a sulfamoyl group, a thioacyl group or a thiocarbamoyl group; $R^3$ represents a hydrogen atom; $R^2$ and $R^3$ may be bonded each other to form a hydrazone structure; a part of L and $R^1$ may be bonded each other to form a hydrazone structure; and n represents 0 or 1.

The silver halide color photographic light-sensitive material containing the compound capable of imagewise releasing a fogging agent represented by the general formula (I) is improved in stability during preservation and has a high contrast and sensitivity. A method of forming a color image using the silver halide color photographic light-sensitive material is also disclosed.

19 Claims, No Drawings ical light-sensitive material containing a com-
SILVER HALIDE COLOR PHOTOGRAPHIC LIGHT-SENSITIVE MATERIAL This is a continuation of application Ser. No. 583,901, filed Feb. 27, 1984, abandoned.

FIELD OF THE INVENTION

The present invention relates to a silver halide color photographic light-sensitive material containing a compound capable of imagewise releasing a fogging agent in which the contrast and sensitivity are increased, the development is accelerated and the stability during preservation is improved, and a method of forming a color image using such a compound.

BACKGROUND OF THE INVENTION

It is well known that color images can be obtained by exposing a silver halide color photographic light-sensitive material to light, followed by a color development during which the reaction between an oxidized aromatic primary amine developing agent and a dye forming coupler takes place. In such a process, the subtractive color process is usually utilized for color reproduction, and cyan, magenta and yellow color images, which are complementary to red, green and blue colors, respectively, are formed. The reaction between a coupler and an oxidation product of a color developing agent proceeds at an active point of the coupler. A coupler having a hydrogen atom at its active point (i.e., 4-equivalent coupler) stoichiometrically requires as an oxidizing agent 4 moles of silver halide having a development center for forming 1 mole of dye through the coupling reaction. On the contrary, a coupler having at its active point a group capable of being released in the form of an anion requires only 2 moles of silver halides having a development center for forming 1 mole of dye (i.e., 2-equivalent coupler). Accordingly, by using a 2-equivalent coupler, the amount of silver halide to be used in a light-sensitive layer can be reduced and the layer per se can be made thinner, so that the time required for the processing of such a light-sensitive material can be shortened and color images obtained therefrom can have an improved sharpness, compared with a light-sensitive material in which a 4-equivalent coupler is used. In addition, the coupling activity of a 2-equivalent coupler with a color developing agent can be widely varied, depending on the property of the releasable group contained therein.

A 2-equivalent coupler capable of releasing a group having a development-inhibiting effect is known and called a development inhibitor releasing coupler (or DIR coupler). Such couplers are capable of inhibiting development in proportion to the quantity of developed silver and, therefore, can be effective for improving graininess, controlling gradation and improving color reproducibility of the image. Couplers of this type can also be used in diffusion transfer processes, wherein their effects upon adjacent layers are utilized.

A 2-equivalent coupler can also be provided with a releasable group containing a diffusible dye portion. This class of couplers, which are referred to as diffusible dye-releasing coupler, can be utilized in a diffusion transfer process in which a dye image is formed from diffused dyes in an image receiving layer.

A certain colored 2-equivalent coupler can also be used to attain a masking effect necessary for color correction of dye images. This class of couplers are referred to as colored coupler.

As mentioned hereinbefore, 2-equivalent couplers can be provided with various functions, depending on the selection of releasable groups contained therein.

On the other hand, regarding the recent trend in the development of silver halide photographic light-sensitive materials, in particular, used for photographing, two major streams can be seen. One is the increase in sensitivity, as typically shown by ASA 400 films, etc. The other is the improvement in image quality to cope with the miniaturization of film sizes. In connection with the former, investigations have been made on a variety of techniques, including, e.g., large size silver halide grains, couplers with higher activities, acceleration of development, etc. However, the increase in sensitivity based on large size silver halide grains seems to be reaching its limit, as reported by G. C. Farnell and J. B. Chanter in *J. Photogr. Sci.*, 9, 75 (1961). Accordingly, this technique is not expected to make much contribution in the future. In addition, the use of large size silver halide grains is accompanied by various disadvantages, such as deterioration in graininess. Couplers having higher activities have also been studied extensively. Such couplers, however, have not made much contribution to sensitivities of silver halide photographic light-sensitive materials, and proved to be disadvantageous for graininess. With regard to acceleration of development, various development accelerators, including hydrazine compounds, have hitherto been attempted in a silver halide emulsion layer or a developing solution therefor mainly with respect to black-and-white photographic light-sensitive materials. However, is most cases, the incorporation of development accelerators into an emulsion layer or a developing solution is accompanied by such disadvantages as increase in fog and deterioration in graininess and hence impractical.

Couplers which imagewise release development accelerators or fogging agents have also been proposed. For example, couplers releasing thiocyanic acid ions which accelerate the solution physical development are disclosed in U.S. Pat. Nos. 3,214,377 and 3,253,924, Japanese Patent Application (OPI) No. 17437/76, etc. Further, couplers releasing acyl hydrazines are described in Japanese Patent Application (OPI) No. 150845/82 and couplers releasing hydroquinone or aminophenol developing agents are described in Japanese Patent Application (OPI) No. 138636/82. However, the development accelerating function or the fogging function of these releasable groups is small and thus the effects can be obtained only when these couplers are used in a large amount. Also, the effects obtained are very small even if the couplers are employed in a large amount. Further, these couplers have the disadvantage in that color mixing occurs and the color reproducibility is degraded and in that the graininess is deteriorated since the releasable groups diffuse into other layers to cause development acceleration or to form fog due to their large diffusibility, when they are incorporated into a certain light-sensitive layer which is sensitive to light of a specific region in the spectrum. Moreover, most of these couplers have low stability and they undesirably cause several deteriorations in photographic properties, for example, increase in fog, desensitization, color contamination, etc., during preservation when they are incorporated into silver halide photographic light-sensitive materials.

SUMMARY OF THE INVENTION

It is, therefore, an object of the present invention to provide a silver halide photographic light-sensitive material having improved sensitivity and graininess.

It is another object of the present invention to provide a silver halide photographic light-sensitive material having a high contrast.

It is a further object of the present invention to provide a silver halide photographic light-sensitive material capable of being processed by a rapid processing.

It is a further object of the present invention to provide a silver halide photographic light-sensitive material having improved stability during preservation.

Other objects of the present invention will be apparent from the following detailed description and examples.

As the results of various investigations, it has now been found that the above described objects of the present invention can be achieved by incorporating a compound represented by the general formula (I) described below into a silver halide photographic light-sensitive material even in a very small amount.

Accordingly, in accordance with the present invention there is provided a silver halide color photographic light-sensitive material comprising a support having thereon a silver halide emulsion layer and a compound represented by the following general formula (I):

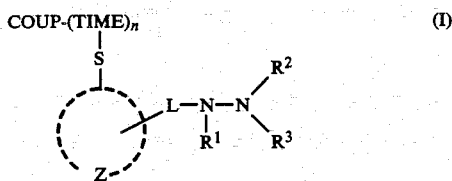

(I)

wherein COUP represents a coupler residue capable of being subjected to a coupling reaction with an oxidation product of an aromatic primary amine developing agent; TIME represents a timing group which is released upon the coupling reaction and subsequently releases

Z represents a monocyclic or condensed heterocyclic ring consisting of a nitrogen atom and a carbon atom; L represents a divalent linking group; $R^1$ represents a hydrogen atom or an alkoxycarbonyl group; $R^2$ represents a hydrogen atom, an alkyl group, an aryl group, a heterocyclic group, an acyl group, a sulfonyl group, an alkoxycarbonyl group, a carbamoyl group, a sulfamoyl group, a thioacyl group or a thiocarbamoyl group; $R^3$ represents a hydrogen atom; $R^2$ and $R^3$ may be bonded each other to form a hydrazone structure; a part of L and $R^1$ may be bonded each other to form a hydrazone structure; and n represents 0 or 1.

DETAILED DESCRIPTION OF THE INVENTION

The present invention relates to a novel class of coupler capable of releasing a fogging agent as a releasable group (foggant releasing coupler or FR couler). Hereinafter the compound according to the present invention is referred to as FR coupler.

Detailed descriptions will hereinafter be given on FR couplers according to the present invention.

In the general formula (I), the hydrazone structure which is formed with a part of L and $R^1$ includes a group of the formula

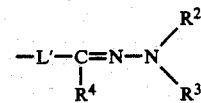

wherein $R^4$ represents a hydrogen atom, an alkyl group or an aryl group; and L' represents a divalent linking group.

The coupler residue represented by COUP includes a residue derived from a cyan, magenta, yellow or non-color-forming coupler. Examples of coupler residues represented by COUP include residues of cyan couplers, such as phenol couplers and naphthol couplers; residues of magenta couplers, such as 5-pyrazolone couplers, pyrazolobenzimidazole couplers, pyrazolotriazole couplers, cyanoacetylcoumarone couplers, open chain acylacetonitrile couplers and indazolone couplers; reisudes of yellow couplers, such as benzoylacetanilide couplers, pivaloylacetanilide couplers, and malondianilide couplers; and residues of non-color-forming couplers, such as open chain or cyclic active methylene compounds (e.g., indanones, cyclopentanones, diesters of malonic acid, imidazolinones, oxazolidines, thiazolinones, etc.).

Of the coupler residues represented by COUP, those which can be preferably used in the present invention include the residues represented by the following general formula (II), (III), (IV), (V), (VI), (VII), (VIII), (IX) or (X):

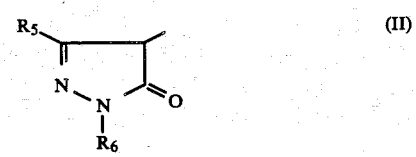

(II)

wherein $R_5$ represents an acylamido group, an anilino group or a ureido group; and $R_6$ represents a phenyl group which may be substituted with one or more substituents selected from a halogen atom, an alkyl group, an alkoxy group or a cyano group.

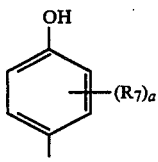

wherein $R_7$ represents a halogen atom, an acylamido group or an aliphatic group; and a represents an integer of 1 to 4.

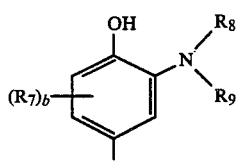

wherein $R_7$ has the same meaning as defined above; $R_8$ and $R_9$ each represents an aliphatic group, an aromatic group, a carbamoyl group or a heterocyclic group, either of $R_8$ and $R_9$ may be a hydrogen atom; and b represents 0 or an integer of 1 to 3.

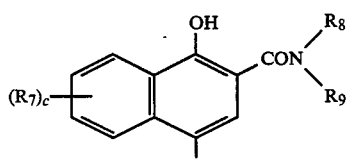

wherein $R_7$, $R_8$ and $R_9$ each has the same meaning as defined above; and c represents 0 or an integer of 1 to 5.

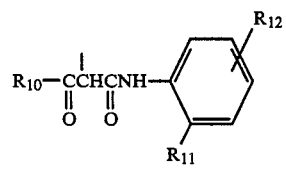

wherein $R_{10}$ represents a tertiary alkyl group or an aromatic group; $R_{11}$ represents a hydrogen atom, a halogen atom or an alkoxy group; and $R_{12}$ represents an acylamido group, an aliphatic group, an alkoxycarbonyl group, a sulfamoyl group, a carbamoyl group, an alkoxy group, a halogen atom or a sulfonamido group.

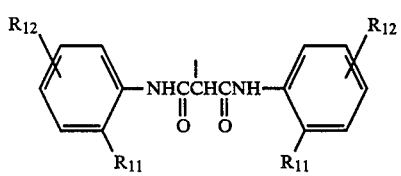

wherein $R_{11}$ and $R_{12}$ each has the same meaning as defined above.

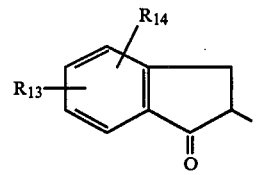

wherein $R_{13}$ represents an aliphatic group, an alkoxy group, a mercapto group, an alkylthio group, an acylamido group, an alkoxycarbonyl group, a sulfonamido group, a carbamoyl group, a sulfamoyl group, an alkoxysulfonyl group, an aryloxysulfonyl group, a acyl group, a diacylamino group, an alkylsulfonyl group or an arylsulfonyl group; and $R_{14}$ represents a hydrogen atom, a halogen atom, an alkoxy group, an acyl group, a nitro group, an alkylsulfonyl group or an arylsulfonyl group; or the group represented by general formula (VIII) above may be in the form of an enol ester thereof.

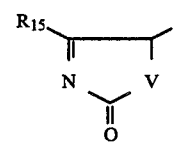

wherein $R_{15}$ represents an aliphatic group or an aromatic group; and V represents an oxygen atom, a sulfur atom or a nitrogen atom.

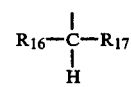

wherein $R_{16}$ and $R_{17}$ each represents a group selected from

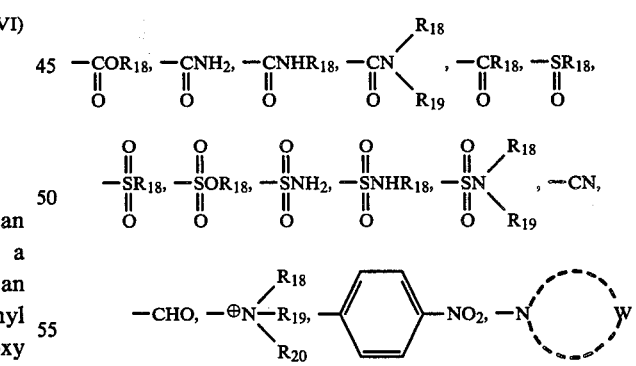

wherein $R_{18}$, $R_{19}$ and $R_{20}$ each represents a hydrogen atom, an aliphatic group, an aromatic group or a heterocyclic group; and W represents a non-metallic atomic group necessary to form a 5-membered or 6-membered ring together with the nitrogen atom; or $R_{16}$ and $R_{17}$ in combination may form a 5-membered or 6-membered ring together with a non-metallic atomic group necessary.

The timing group represented by TIME in the general formula (I) includes a group which is released from COUP upon the coupling reaction and subsequently releases a group of

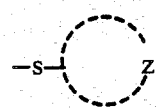

upon an intramolecular displacemnent reaction as described in U.S. Pat. No. 4,248,962, Japanese Patent Application (OPI) No. 57837/82, etc., a group which releases a group of

upon an electron transfer reaction via a conjugated system as described in British Pat. No. 2,072,363A, Japanese Patent Application (OPI) Nos. 154234/82 and 188035/82, etc., or a group of coupling component capable of releasing a group of

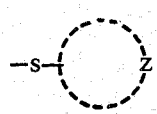

upon the coupling reaction with the oxidation product of an aromatic primary amine developing agent as described in Japanese Patent Application (OPI) No. 111536/82, etc.

The timing group represented by TIME in Japanese Patent application (OPI) No. 56837/82 represents a group represented by a

portion being present in the following general formula:

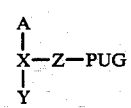

In the above general formula, A represents a component capable of reacting with the oxidation product of a color developing agent, PUG represents a photographically useful group, Y represents a nucleophilic group precursor, which may be connected with X to form a ring, and Z represents an electrophilic group. X is a group by which Y is three-dimensionally connected with Z, and it is connected with A at a position capable of being substituted with the oxidation product of the color developing agent. After the bond between A and X is cleaved, Y is changed to a nucleophilic group which causes an intramolecular nucleophilic displacement reaction with a ring closure with Z, whereby PUG is released.

The groups represented by X, Y and Z in the above-described general formula are groups capable of releasing the photographically useful group at a controlled timing, which are hereinafter called a timing group.

To explain the above-described compounds in view of the basic behavior, the A component can include any components capable of releasing an

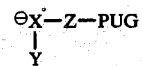

group upon reaction with the oxidation product of the color developing agent, examples of which components include the conventional couplers capable of forming a colored substance upon reaction with the oxidation product of the color developing agent and the compounds capable of forming a colorless substance upon reaction with the oxidation product of the color developing agent. The A component need not be stabilized (have a ballast group), but it may be stabilized with an oil-soluble group or an aliphatic group. An

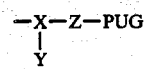

group is connected with the A component at a position where the A component reacts with the oxidation product of the color developing agent. Therefore, after the compound represented by the above-described general formula reacted with the oxidation product of the color developing agent, the

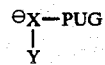

group is released. On the other hand, a part of the released

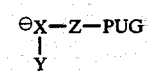

group is present as an

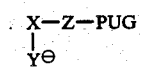

group through the conjugated system in X because of the occurrence of the delocalization of electrode. Consequently, Y which is the nucleophilic precursor is changed to the nucleophilic group which can cause an intramolecular nucleophilic displacement reaction with Z which is an electrophilic group, whereby PUG is ultimately released. Thus, X is a group by which Y and Z are related with the three-dimensional position.

Further, the timing group represented by TIME in Japanese patent application (OPI) No. 188035/82 represents a group represented by a

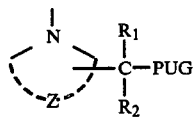

portion being present in the following general formula:

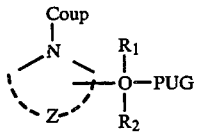

In the above formula, Coup represents a coupling component capable of coupling with the oxidation product of a color developing agent, $R_1$ and $R_2$ each represents a structural element capable of formng a 5-membered heterocyclic ring (inclusive of one forming a condensed ring), and Coup is connected with the heterocyclic ring at a position capable of being substituted with the oxidation product of the color developing agent. PUG represents a photographically useful group capable of being released, after the heterocyclic ring was released from Coup.

British Pat. No. 2,072,363 A discloses that the compounds which are preferable for use are represented by the formula as follows:

$$A\text{-TIME-PUG} \qquad (1)$$

where "A" is the coupler group capable of coupling reaction with the oxidized color developing agent, "TIME" the timing group and "PUG" the photographically useful group.

In the above formula, any compound may be used for the coupler group A insofar as it can react with the oxidized color developing agent to release the group -TIME-PUG. Examples of the coupler group include one which will form a colored product or a colorless product on coupling reaction with the oxidized color developing agent. The coupler group A may have no ballasting group or may be ballasted with an oil soluble or aliphatic group or groups. The group -TIME-PUG is attached to the component A at the coupling site, which is capable of coupling reaction with the oxidized color developing agent. The timing group joining the PUG and the component A may be any organic group such that it can be cleaved from the PUG as a result of an electron transfer along a conjugated system toward PUG after the group -TIME-PUG is cleaved from the component A.

In British Pat. No. 2,072,363 A, the term "conjugated system" refers to the form of bonding well known in chemistry, namely the one in which a single bond and a double or triple bond appear alternatively in the chemical formula. Accordingly, it is assumed that the lone pair electron on the fragment -TIME-PUG cleaved from the component A is transferred along a conjugated system to ultimately break the bond between the TIME and PUG.

Examples of the timing group are formulated in the following formula:

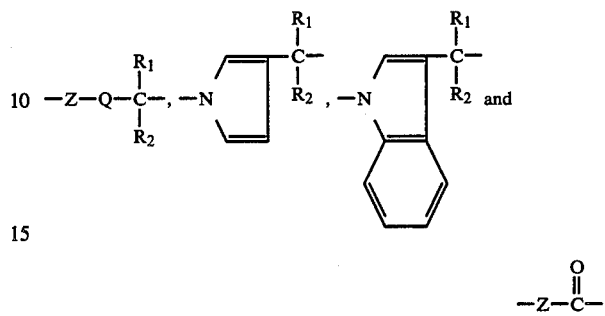

wherein the left hand side is attached to the coupler group, Z is

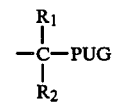

$R_1$, $R_2$ and $R_3$ are individually a hydrogen atom, alkyl or aryl group, Q is a 1,2- or 1,4-phenylene or naphthylene group. The phenylene or naphthylene may have a substituent such as halogen atom, alkyl, alkoxy, —CN, —$NO_2$, —NHCOR or —COOR wherein R is alkyl.

In case the TIME group forms quinomethide or naphthoquinomethide on the final cleavage, the compound includes one represented by the following general formula:

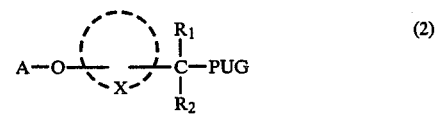

where "A" and "PUG" are the same as defined in the general formula (1) of British Pat. No. 2,072,363 A while "X" represents atoms necessary to complete a substituted or nonsubstituted benzene or naphthalene nucleus and "$R_1$" and "$R_2$" individually represent a hydrogen atom, alkyl group or aryl group, with the group $$-\underset{R_2}{\underset{|}{\overset{R_1}{\overset{|}{C}}}}-\text{PUG}$$

being joined at the para or ortho position relative to the oxygen atom.

The compound as represented by the above general formula (2) of British Pat. No. 2,072,363 A is cleaved as it reacts with the oxidized color developing agent, first forming a compound as represented by the following general formula (3), which is then recleaved through an electron transfer along the conjugated system to form a compound as represented by the following general formula (4) while releasing the PUG:

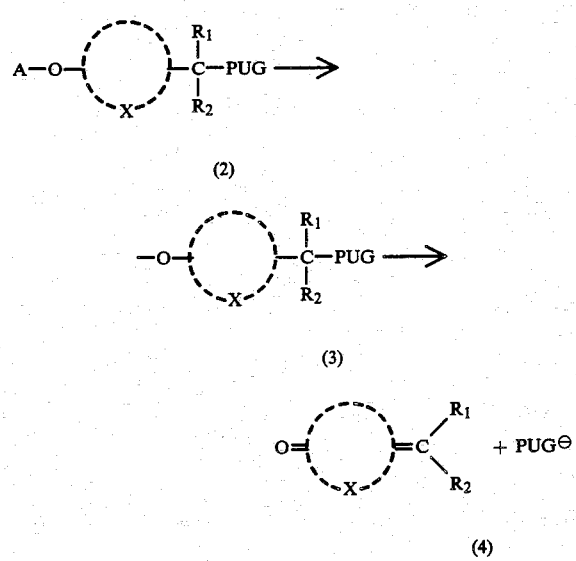

(2)

(3)

(4)

The above compound (4) is called either quinonemethide or naphthoquinonemethide.

Next, as a compound of British Pat. No. 2,072,363 A, a compound comprising a timing group which will ultimately form a quinomethide compound and phenylmercaptotetrazole as the PUG is selected to illustrate the process diagrammatically:

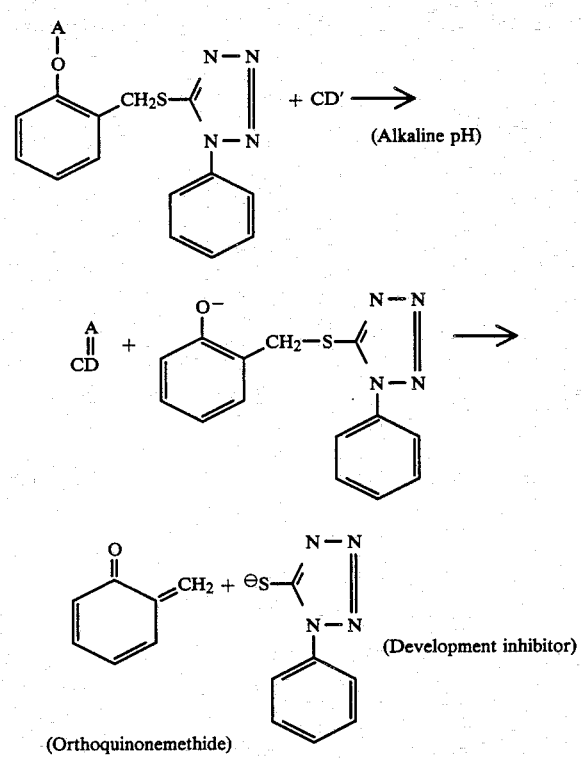

where "CD" represents the oxidized color developing agent.

In the above diagram, upon the coupling reaction the compound cleaves to release the timing group bonded to the photographically useful group (development inhibitor in this case), which is then recleaved by an electron transfer along the conjugated system as indicated by arrows to form orthoquinonemethide while releasing the development inhibitor.

Further, the process is again illustrated diagrammatically below for a compound that uses a timing group other than the one used above as another example:

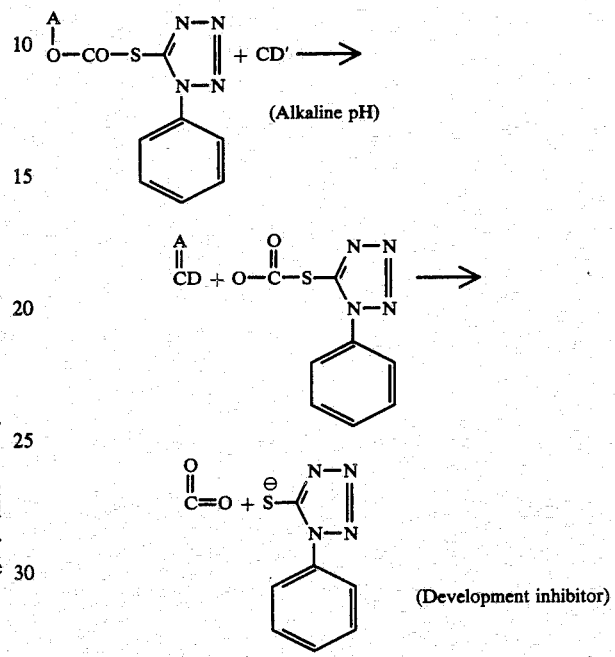

where "A" and "CD" are the same as defined previously. Also in this case, in the fragment that is released from the compound after its reaction with CD' a lone pair electron located on the oxygen atom is conjugated with the carbonyl π electrons.

The coupler of Japanese Patent Application (OPI) No. 111536/82 has the following structure:

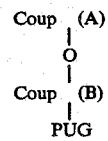

wherein Coup (A) represents a coupling component (A) and Coup (B) a coupling component (B), Coup (A) being bonded to the oxygen atom O at the position capable of forming a colored or a colorless compound through coupling with an oxidized form of a color forming developing agent, Coup (B) being bonded to the oxygen atom in the form such that it can be made for the first time capable of coupling with an oxide of a color forming developing agent by being released from Coup (A) upon coupling of Coup (A), and PUG being bonded at the position capable of coupling with an oxide of a color forming developing agent of Coup (B) and in the form such that it can be released from Coup (B) by said coupling.

The mechanism of action of the coupler for photography represented by the above formula is schematically illustrated below:

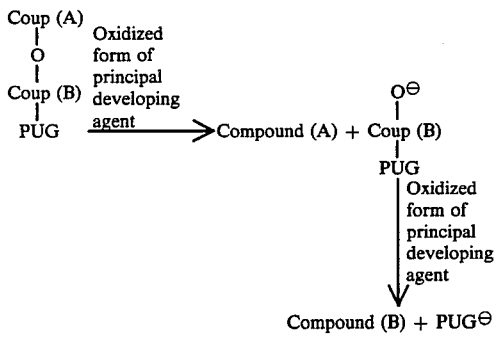

wherein Coup (A), Coup (B) and PUG are the same as defined in the above formula; Compound (A) and Compound (B) are products formed by coupling of Coup (A) and Coup (B), respectively, with an oxidized form of a developing agent.

As the coupling component (A) and the coupling component (B) of the present invention, there may generally be employed residues of yellow, cyan and magenta couplers conventionally used for silver halide photographic photosensitive materials. Among them, there are included those which can form colorless compounds through coupling with an oxidized form of a color forming developing agent and also those which can form colored compounds. Examples of those capable of forming colorless compounds through coupling are acetophenone derivative residues and indanone derivative residues, while those capable of forming colored compounds through coupling may include various residues of couplers as enumerated below.

As yellow couplers are concerned, there may be mentioned benzoyl acetoanilide type yellow couplers or pivaaloyl acetanilide type yellow couplers. As for magenta couplers, there are various magenta couplers such as pyrazolone type magenta couplers and indazolone type magenta couplers.

Further in the case of cyan couplers, there are naphthol type of phenol type couplers.

As a photographically useful group PUG, there may be employed any group which can cause a photographically advantageous effect in a photographic element.

More preferably, in the above formula, the moiety excluding Coup (A) may be a diffusible compound residue.

Japanese Patent Application (OPI) No. 154234/82 discloses a compound used in silver halide photographic material having the following structure:

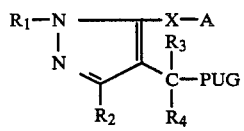

wherein A represents a group being capable of leaving under photographic treatment, X represents —O—, —S— or

(wherein $R_5$ represents a hydrogen atom, an alkyl group, an aryl group, an acyl group or a sulfonyl group) and can form a condensed ring together with $R_1$, $R_1$ represents a hydrogen atom, an alkyl group, an aryl group, an acyl group, a sulfonyl group, an alkoxy group, an amino group, a carbamide, a sulfonamide, a carboxyl group, an alkoxycarbonyl group, a carbamoyl, a cyano group or a halogenized alkyl group, $R_3$ and $R_4$ represent a hydrogen atom, alkyl group or an aryl group, PUG represents a photographically useful group connecting with a carbon atom substituted at the fourth position of pyrazole ring. PUG contains, for example, groups for silver halide-solving agent, a hardener, a fogging agent, a developer, a development accelerator, a development inhibitor, but a group for a development inhibiter is most preferable.

The heterocyclic ring represented by Z in the general formula (I) is preferably a 5-membered or 6-membered ring. Examples of the heterocyclic rings include pyrrole, imidazole, pyrazole, triazole, tetrazole, benzimidazole, benzopyrazole, indole, imidazoline, pyrazoline, pyridine, pyrimidine, pyrazine, pyridazine, triazine, imidazotetrazole, pyrazolotriazole, tetraazaindene, pentaazaindene, etc.

The divalent linking group represented by L in the general formula (I) can be selected from conventionally used divalent groups including, for example, an alkylene group, an alkenylene group, a phenylene group, a naphthylene group, —O—, —S—, —SO—, —SO$_2$—, —N=N—, a carbonyl group, an amido group, a thioamido group, a sulfonamido group, a ureido group, a thioureido group, a heterocyclic group, etc.

Preferred examples for $R^1$ include a hydrogen atom or an alkoxycarbonyl group (for example, a methoxycarbonyl group, a phenoxycarbonyl group, etc.). Preferred examples for $R^2$ include a hydrogen atom, an alkyl group (for example, a methyl group, an ethyl group, etc.), an aryl group (for example, a phenyl group, a p-tolyl group, a 3-methoxyphenyl group, a naphthyl group, etc.), a heterocylic group (for example, a 2-pyridyl group, a triazyl group, a 2-furyl group, a 2-thienyl group, a 2-quinolyl group, etc.), an acyl group (for example, an acetyl group, a formyl group, a chloroacetyl group, a propionyl group, a trifluoroacetyl group, a heptafluorobutanoyl group, a benzoyl group, etc.), a sulfonyl group (for example, a methanesulfonyl group, a benzenesulfonyl group, etc.), an alkoxycarbonyl group (for example, a methoxycarbonyl group, an ethoxycarbonyl group, etc.), a carbamoyl group (for example, an N,N-dimethylcarbamoyl group, etc.), a sulfamoyl group (for example, an N,N-dimethylsulfamoyl group, etc.), a thioacyl group (for example, a thioacetyl group, a thiobenzoyl group, etc.) or a thiocarbamoyl group (for example, an N,N-dimethylthiocarbamoyl group, etc.). Preferred example of $R^3$ includes a hydrogen atom. $R^2$ and $R^3$ in the general formula (I) may be bonded each other to form a hydrazone structure.

Preferred specific examples of the group represented by
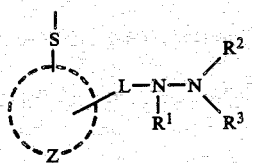
are set forth below, but the present invention should not be construed as being limited thereto.
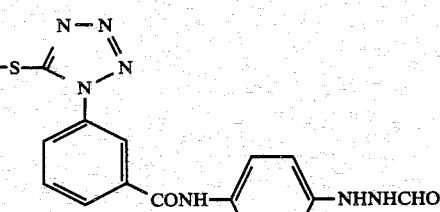
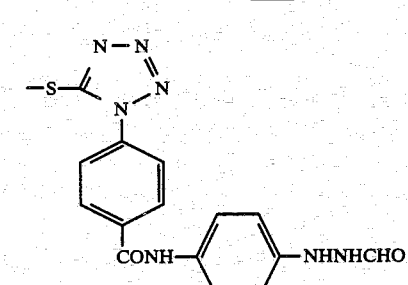
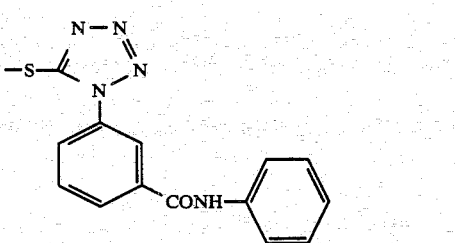
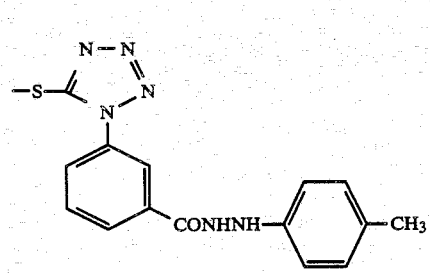
-continued
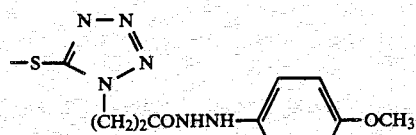
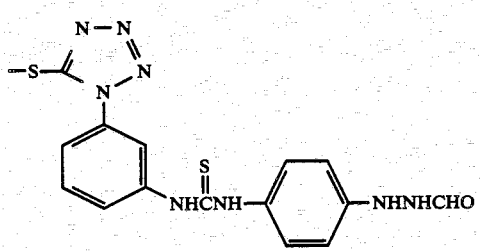
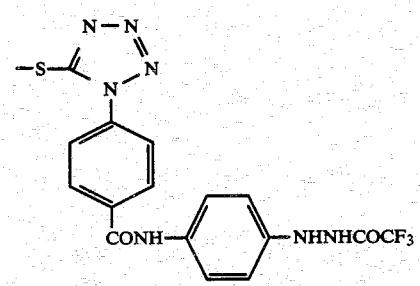
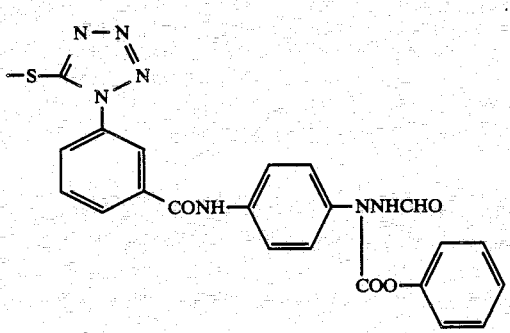
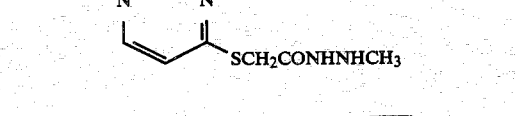
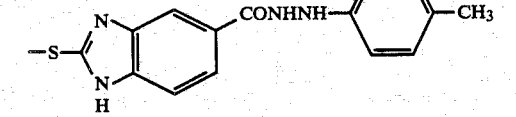

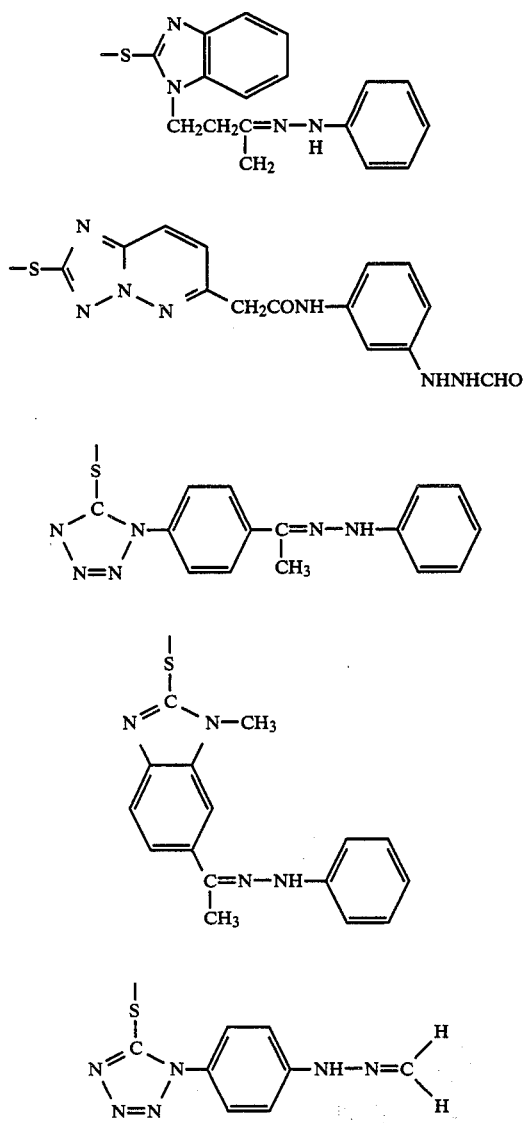
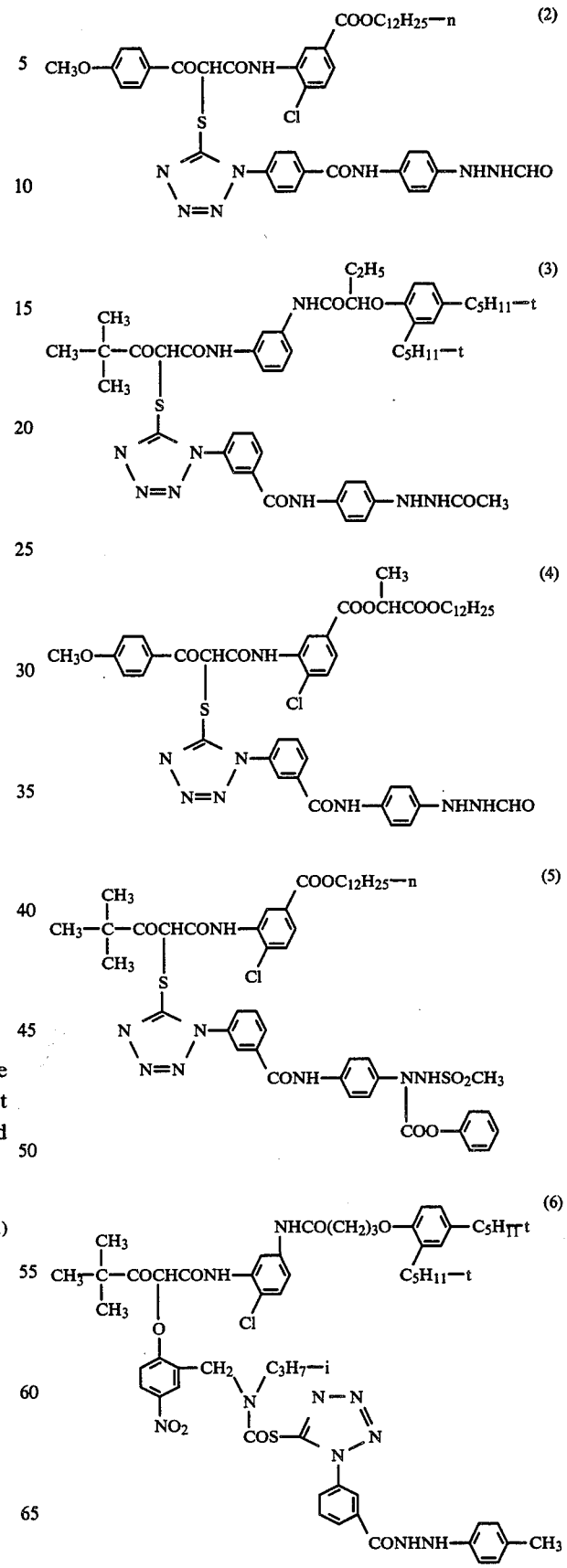
Specific examples of the compound according to the present invention are set forth below, but the present invention should not be construed as being limited thereto.
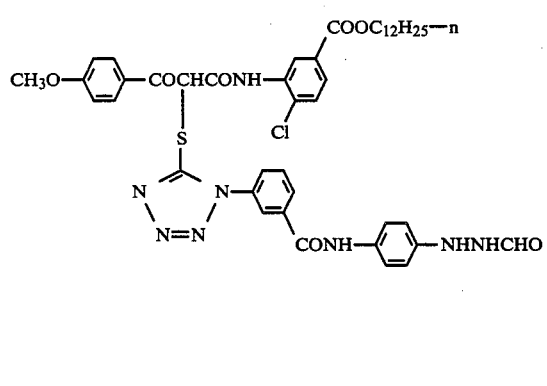
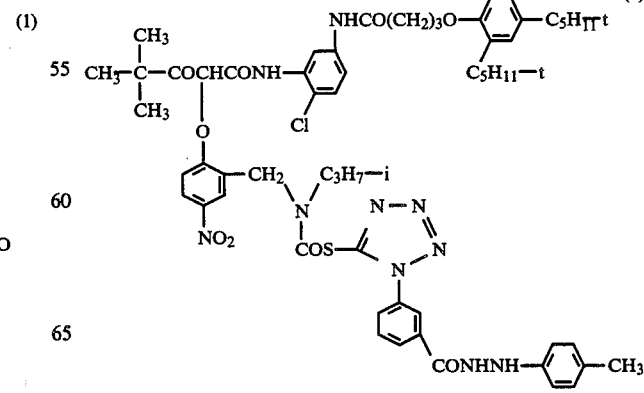

-continued
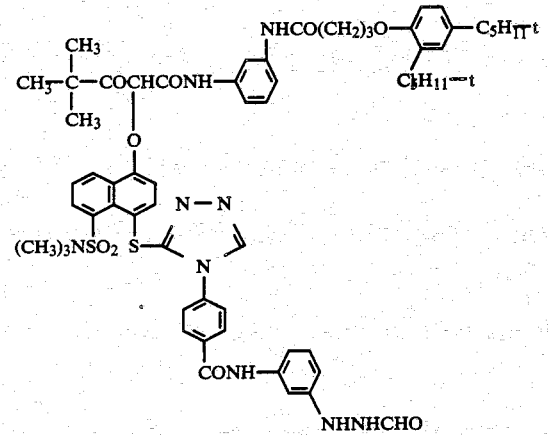
(7)
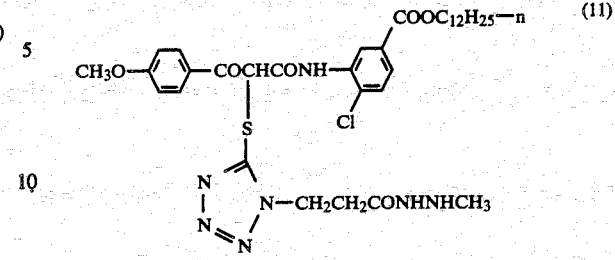
(11)
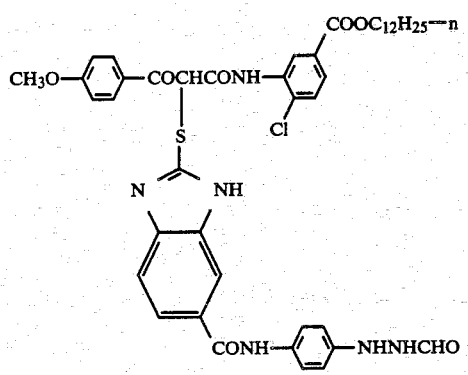
(8)
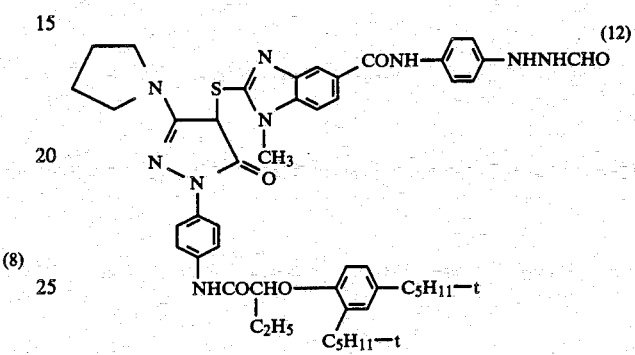
(12)
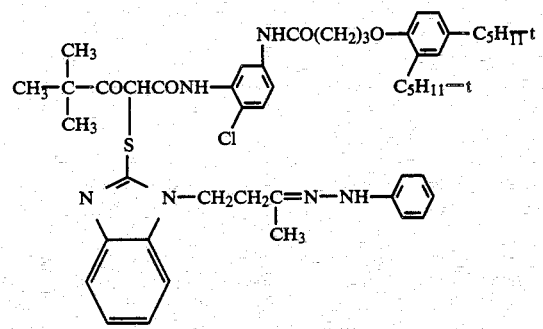
(9)
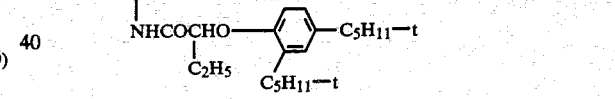
(13)
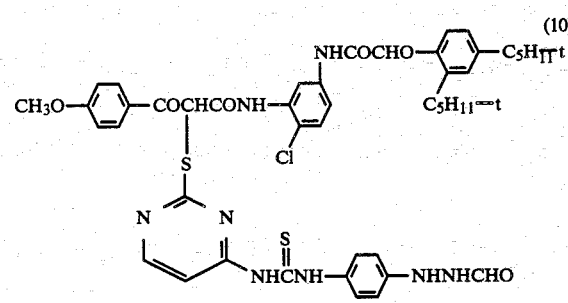
(10)
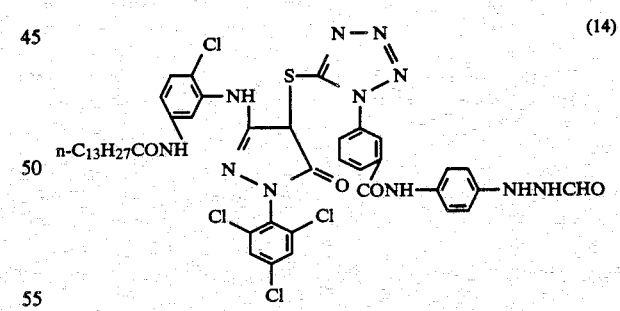
(14)
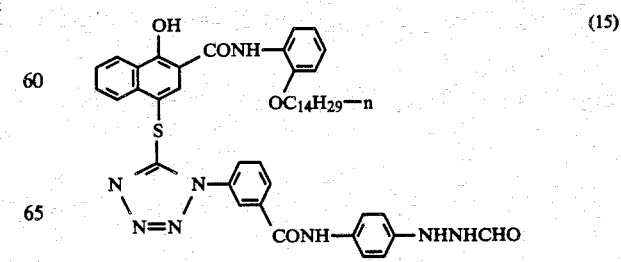
(15)

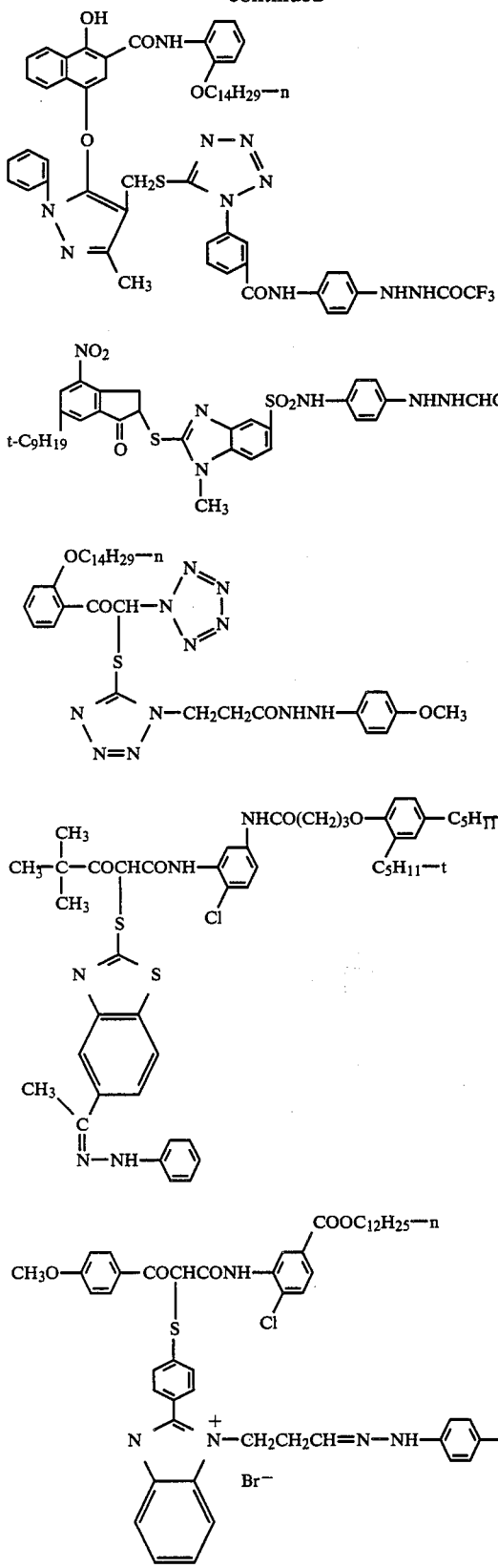

The compound according to the present invention can be synthesized, for example, along the reaction scheme as described in Japanese Patent Application (OPI) No. 150845/82. Examples of synthesis are set forth below.

SYNTHESIS EXAMPLE 1

Synthesis of Compound (1)

82.5 g of ethyl m-aminobenzoate was dissolved in 500 ml of toluene and to the solution was added dropwise 83.4 g of N,N-diethylthiocarbamoyl chloride at room temperature with stirring over a period of about 1 hour. The mixture was then refluxed by heating for 5 hours. The toluene was distilled off under reduced pressure, to the residue was added 300 ml of ethyl acetate and the ethyl acetate solution was washed with water. The ethyl acetate was distilled off under reduced pressure and the residue was further subjected to vacuum distillation to obtain 80 g of ethyl m-isothiocyanatobenzoate as oily product. Boiling Point: 125° C./0.6 mm Hg. Yield: 77%.

500 ml of water was added to a mixture of 69 g of ethyl m-isothiocyanatobenzoate and 26 g of sodium azide and the mixture was refluxed by heating for 2 hours. After removing the insoluble material deposited by filtration, concentrated hydrochloric acid was added to the filtrate whereby the filtrate was acidified (pH: about 2). The crystals of 1-(3-ethoxycarbonylphenyl)-5-mercaptotetrazole thus deposited were collected by filtration, to which were added 30 g of sodium hydroxide and 300 ml of water and the mixture was heated to 70° C. and stirred for 30 minutes. The reaction solution was neutralized with concentrated hydrochloric acid and the crystals thus deposited were collected by filtration. By recrystallization of the crude crystals from methanol 32 g of 1-(3-carboxyphenyl)-5-mercaptotetrazole was obtained. Yield: 42%. Melting Point: 181° to 182° C.

33 g of α-chloro-α-(4-methoxybenzoyl)-2-chloro-5-dodecyloxycarbonylacetanilide and 16 g of 1-(3-carboxyphenyl)-5-mercaptotetrazole were dispersed in 200 ml of chloroform and to which was added dropwise 10 ml of triethylamine at room temperature over a period of about 30 minutes. After stirring for 3 hours the chloroform solution washed with water and concentrated under reduced pressure. The residue was crystallized from methanol to obtain 37.4 g of α-(4-methoxybenzoyl)-α-[1-(3-carboxyphenyl)-5-tetrazolylthio]-2-chloro-5-dodecyloxycarbonylacetanilide. Yield: 85%. Melting Point: 155° to 162° C.

Then, 1-formyl-2-(4-aminophenyl)hydrazide was synthesized according to the process described in Japanese Patent Application (OPI) No. 74729/79. Namely, to 1.6 l of acetonitrile, 459 g of 4-nitrophenylhydrazine was added with stirring, and 322 g of formic acid was then gradually added thereto to obtain a homogeneous solution. After 20 minutes, crystals were deposited. After carried out the reaction at a temperature of 80° C. for further 2 hours, the mixture was cooled and filtered to separate crystals. The crystals were washed with acetonitrile and dried to obtain 495 g of 1-formyl-2-(4-nitrophenyl)hydrazine. Melting Point: 184° to 186° C.

30 g of 1-formyl-2-(4-nitrophenyl)hydrazine was then catalytically reduced at room temperature in 1.6 l of ethanol using palladium-carbon as a catalyst. The reacting solution was filtered, and the filtrate was evaporated to dryness to obtain 20.5 g of 1-formyl-2-(4-aminophenyl)hydrazine as light brown solid. Melting Point: 123° to 125° C.

22.1 g of α-(4-methoxybenzoyl)-α-[1-(3-carboxyphenyl)-5-tetrazolylthio]-2-chloro-5-dodecyloxycarbonylacetanilide and 5.5 g of 1-formyl-2-(4-aminophenyl)hydrazine were dissolved in 75 ml of DMF and to the solution was added dropwise 5 ml of a DMF solution containing 6.2 g of dicyclohexylcarbodiimide under nitrogen atmosphere while cooling at 10° C. or below. The mixture was further sitrred at room temperature for 2 hours and filtered. To the filtrate was added water and extracted with ethyl acetate. The ethyl acetate was distilled off under reduced pressure, the residue was crystallized with methanol to obtain 13 g of the desired Compound (1). Yield: 50%. Melting Point: 175° to 181° C.

Elementary Analysis for $C_{44}H_{49}N_8O_7SCl$: Calcd.: H: 5.68%, C: 60.78%, N: 12.89%. Found: H: 5.72%, C: 60.75%, N: 12.73%.

SYNTHESIS EXAMPLE 2

Synthesis of Compound (2)

82.5 g of ethyl p-aminobenzoate was dissolved in 500 ml of toluene, to the solution was added 83.4 g of N,N-diethylthiocarbamoyl chloride and the mixture was refluxed by heating for 8 hours. After cooling with ice, 100 ml of concentrated hydrochloric acid was added to the reaction mixture and then the toluene layer was separated and washed with water. The toluene was distilled off under reduced pressure and the residual oily product was crystallized from methanol to obtain 77.1 g of ethyl p-isothiocyanatobenzoate. Yield: 74.5%. Melting Point: 52° C.

31 g of p-isothiocyanatobenzoate and 11.7 g of sodium azide were dispersed in 300 ml of water and the mixture was refluxed by heating for 5 hours. The reaction mixture was cooled to room temperature to which was added concentrated hydrochloric acid whereby the mixture was acidified (pH: about 2). The crystals of 1-(4-ethoxycarbonylphenyl)-5-mercaptotetrazole thus deposited were collected by filtration, to which was added 25 g of sodium hydroxide and 500 ml of water and the mixture was stirred at 70° C. for 30 minutes. After cooling to room temperature, the reaction mixture was neutralized by adding concentrated hydrochloric acid and the crystals thus deposited were collected by filtration. By recrystallization from methanol 40 g of 1-(4-carboxyphenyl)-5-mercaptotetrazole was obtained. Yield: 48%. Melting Point: 198° C.

33 g of α-chloro-α-(4-methoxybenzoyl)-2-chloro-5-dodecyloxycarbonylacetanilide and 16 g of 1-(4-carboxyphenyl)-5-mercaptotetrazole were dispersed in 200 ml of chloroform to which was added dropwise 10 ml of triethylamine at room temperature over a period of about 30 minutes. After stirring for 3 hours the chloroform solution was washed with water and concentrated under reduced pressure. The residue was recrystallized from methanol to obtain 41.2 g of α-(4-methoxybenzoyl)-α-[1-(4-carboxyphenyl)-5-tetrazolylthio]-2-chloro-5-dodecyloxycarbonylacetanilide. Yield: 93%. Melting Point: 172° to 174° C.

22.1 g of α-(4-methoxybenzoyl)-α-[1-(4-carboxyphenyl)-5-tetrazolylthio]-2-chloro-5-dodecyloxycarbonylacetanilide and 5.5 g of 1-formyl-2-(4-aminophenyl)hydrazine were dissolved in 75 ml of DMF and to the solution was added dropwise 5 ml of a DMF solution containing 6.2 g of dicyclohexylcarbodiimide under nitrogen atmosphere while cooling at 10° C. or below. The mixture was stirred at room temperature for 1 hours and filtered. The filtrate was poured into 1 l of methanol and the crystals thus deposited were collected by filtration to obtain 12.8 g of the desired Compound (2). Yield: 49%. Melting Point: 177° C.

Elementary Analysis for $C_{44}H_{49}N_8O_7SCl$ Calcd.: H: 5.68%, C: 60.78%, N: 12.89%. Found: H: 5.74%, C: 60.66%, N: 12.92%.

SYNTHESIS EXAMPLE 3

Synthesis of Compound (4)

α-(4-methoxybenzoyl)-α-[1-(3-carboxyphenyl)-5-tetrazolylthio]-2-chloro-5-(1-dodecyloxycarbonylethyl)oxycarbonylacetanilide was obtained in the same manner as described in Synthesis Example 1. Yield: 86%. Melting Point: 138° to 140° C.

Using 8.08 g of α-(4-methoxybenzoyl)-α-[1-(3-carboxyphenyl)-5-tetrazolylthio]-2-chloro-5-(1-dodecyloxycarbonylethyl)oxycarbonylacetanilide and 1.81 g of 1-formyl-2-(4-aminophenyl)hydrazine, 4.9 g of the desired Compound (4) was obtained in the same manner as described in Synthesis Example 1. Yield: 52%. Melting Point: 167° to 171° C.

Elementary Analysis for $C_{47}H_{53}N_8O_9SCl$: Calcd.: H: 5.67%, C: 59.95%, N: 11.90%. Found: H: 5.50%, C: 59.78%, N: 11.91%.

SYNTHESIS EXAMPLE 4

Synthesis of Compound (8)

30.4 g of 3,4-diaminobenzoic acid, 50 g of carbon disulfide and 50 g of triethylamine were dissolved in 200 ml of dioxane and the solution was refluxed by heating for 5 hours. The reaction mixture was cooled to room temperature, the crystals thus deposited were collected by filtration and recrystallized from water to obtain 14 g of 2-mercapto-5-carboxybenzimidazole. Melting Point: above 250° C.

3.9 g of 2-mercapto-5-carboxybenzimidazole and 3 ml of triethylamine were dissolved in 50 ml of DMF and to the solution was added dropwise 50 ml of a DMF solution containing 11 g of α-chloro-α-(4-methoxybenzoyl)-2-chloro-5-dodecyloxycarbonylacetanilide at 15° C. over a period of 30 minutes. The reaction mixture was further stirred at room temperature for 2 hours and then poured into 1 liter of water. The crystals thus deposited were collected by filtration and recrystallized from methanol to obtain 11 g of α-(4-methoxybenzoyl)-α-(5-carboxy-2-benzimidazolylthio)-2-chloro-5-dodecyloxycarbonylacetanilide. Yield: 77.6%. Melting Point: 190° to 205° C. 11 g of α-(4-methoxybenzoyl)-α-(5-carboxy-2-benzimidazolylthio)-2-chloro-5-dodecyloxycarbonylacetanilide, 2.6 g of 1-formyl-2-(4-aminophenyl)- hydrazine and 0.1 g of 4-dimethylaminopyrimidine were dissolved in 50 ml of DMF and to the solution was added dropwise 5 ml of a DMF solution containing 3.2 g of dicyclohexylcarbodiimide with stirring at room temperature. The mixture was further stirred at room temperature for 2 hours and then at 50° C. for 30 minutes. After cooling with water, dicyclohexylurea formed was removed by filtration and the filtrate was poured into 500 ml of water. The crystals thus deposited were collected by filtration and purified with 50 ml of hot ethanol to obtain 8.5 g of the desired Compound (8). Yield: 65%. Melting Point: 244° to 247° C.

Elementary Analysis for $C_{44}H_{49}N_6O_7ClS$: Calcd.: H: 5.87%, C: 62.81%, N: 9.99%. Found: H: 5.91%, C: 62.74%, N: 9.98%.

SYNTHESIS EXAMPLE 5

Synthesis of Compound (14)

15 g of 3-(2-chloro-5-tetradecanamidoanilino)-1-(2,4,6-trichlorophenyl)-2-pyrazolin-5-one and 5.4 g of 1-(3-carboxyphenyl)-5-mercaptotetrazole were dissolved in 100 ml of DMF and to the solution was added dropwise at room temperature 20 ml of a DMF solution containing 4.9 g of N-bromosuccinimide. After stirring for 30 minutes, 500 ml of water was added to the mixture which was extracted with ethyl acetate. The ethyl acetate was distilled off under reduced pressure and the residue was crystallized from a solvent mixture of ethyl acetate and acetonitrile to obtain 14 g of 3-(2-chloro-5-tetradecanamidoanilino)-1-(2,4,6-trichlorophenyl)-4-[1-(3-carboxyphenyl)-5-tetrazolylthio]-2-pyrazolin-5-one. Yield: 68%. Melting Point: 155° to 165° C.

8.3 g of 3-(2-chloro-5-tetradecanamidoanilino)-1-(2,4,6-trichlorophenyl)-4-[1-(3-carboxyphenyl)-5-tetrazolylthio]-2-pyrazolin-5-one and 1.66 g of 1-formyl-2-(4-aminophenyl)hydrazine were dissolved in 50 ml of DMF and to the solution was added dropwise at room temperature 5 ml of a DMF solution containing 2.1 g of dicyclohexylcarbodiimide. After stirring at room temperature for 2 hours, dicyclohexylurea formed was removed by filtration and to the filtrate was added 200 ml of water. The crystals thus deposited were collected by filtration and recrystallized from a solvent mixture of ethyl acetate and methanol to obtain 5.6 g of the desired Compound (14). Yield: 58%. Melting Point: 175° to 181° C.

Elementary Analysis for $C_{44}H_{47}N_{11}O_4SCl_4$: Calcd.: H: 4.90%, C: 54.61%, N: 15.92%. Found: H: 4.94%, C: 54.44%, N: 15.88%.

SYNTHESIS EXAMPLE 6

Synthesis of Compound (15)

22.8 g of 2-(2-tetradecyloxyphenyl)carbamoyl-1-naphthol was dissolved in 100 ml of dichloromethane and to the solution was added dropwise at room temperature a dichloromethane solution of the sulfenyl chloride prepared from 25 g of 1-(3-ethoxycarbonylphenyl)-5-mercaptotetrazole and 13.5 g of sulfuryl chloride. After the completion of the addition, the mixture was stirred for 5 hours and the dichloromethane solution was washed with an aqueous solution of sodium hydrogencarbonate and then with water. The dichloromethane was distilled off under reduced pressure and the residue was crystallized from methanol to obtain 26.9 g of 2-(2-tetradecyloxyphenyl)carbamoyl-4-[1-(3-ethoxycarbonylphenyl)-5-tetrazolylthio]-1-naphthol. Yield: 74.3%. Melting Point: 88° to 90° C.

19.5 g of 2-(2-tetradecyloxyphenyl)-4-[1-(3-ethoxycarbonylphenyl)-5-tetrazolylthio]-1-naphthol was added to 50 ml of a methanol solution containing 5.3 g of potassium hydroxide and the mixture was stirred at 40° to 50° C. for 30 minutes. 10 ml of concentrated hydrochloric acid was diluted with 500 ml of water into which was poured the reaction solution. The crystals thus deposited were collected by filtration and recrystallized from methanol to obtain 16.1 g of 2-(2-tetradecyloxyphenyl)carbamoyl-4-[1-(3-carboxyphenyl)-5-tetrazolylthio]-1-naphthol. Yield: 86%. Melting Point: 136° to 138° C.

13.9 g of 2-(2-tetradecyloxyphenyl)carbamoyl-4-[1-(3-carboxyphenyl)-5-tetrazolylthio]-1-naphthol and 3.0 g of 1-formyl-2-(4-aminophenyl)hydrazine were dissolved in 20 ml of DMF and to the solution was added dropwise with stirring 5 ml of a DMF solution containing 4.1 g of dicyclohexylcarbodiimide at 0° C. under nitrogen atmosphere. After the completion of the addition, the mixture was stirred for 2 hours and then further stirred at room temperature for 2 hours. Dicyclohexylurea formed was removed by filtration and the filtrate was poured into 1.5 liters of water. The crystals thus deposited were collected by filtration and dissolved in 50 ml of DMF. After treating with active carbon the DMF solution was poured into 400 ml of methanol and the crystals thus deposited were collected by filtration to obtain 9.2 g of the desired Compound (15). Yield: 55.5%. Melting Point: 173° to 180° C.

Elementary Analysis for $C_{46}H_{52}N_8O_5S$: Calcd.: H: 6.32%, C: 66.64%, N: 13.51%. Found: H: 6.27%, C: 66.53%, N: 13.35%.

The couplers according to the present invention can be used for any kind of usual silver halide color photographic light-sensitive materials, including, for example, color negative films, color papers, color positive films, color reversal films for slides, color reversal films for motion picture and color reversal films for television, etc. The couplers can be particularly effective for color negative or reversal films which are required to possess both high sensitivities and high image qualities.

Since the couplers according to the present invention are effective even when they are used in a small amount, they can be incorporated into any of cyan coupler containing layer, magenta coupler containing layer and yellow coupler containing layer.

With the recent steep rise in the price of silver, which is a raw material for photographic light-sensitive materials, reducing the amount of silver to be used in the photographic light-sensitive materials has become very important, in particular, in the case of X-ray films which require the use of large quantities of silver. From this point of view, it has been proposed to make use of dyes in X-ray films, for example, through the incorporation of a black color-forming coupler (see, e.g., U.S. Pat. Nos. 3,622,629, 3,734,735 and 4,126,461 and Japanese Patent Application (OPI) Nos. 42725/77, 105247/80 and 105248/80) or of a combination of couplers that form three different colors (see, e.g., *Research Disclosure*, Vol. 171, No. 17123). The couplers according to the present invention can be used with particular effectiveness in such X-ray films as they can contribute much for more effective use of silver and, at the same time, faster processing thereof.

The photographic emulsion layers of the photographic light-sensitive materials of the present invention can be incorporated, in addition to the couplers according to the present invention, with conventional color-forming couplers, i.e., compounds capable of forming color upon oxidative coupling with aromatic primary amine developing agents (e.g., phenylenediamine derivatives, aminopheol derivatives, etc.) during the course of color development processing. Examples of such couplers include magenta couplers, such as 5-pyrazolone couplers, pyrazolobenzimidazole couplers, cyanoacetylcoumarone couplers and open chain acylacetonitrile couplers; yellow couplers, such as acylacetamide couplers (e.g., benzoylacetanilides, pivaloylacetanilides, etc.); and cyan couplers, such as naphthol couplers and phenol couplers. It is preferable to use couplers containing a hydrophobic group (so-called ballast group) within the molecule or polymeric non-diffusible couplers. They may be either 2-equivalent or 4-equivalent couplers. It is also possible to use couplers capable, upon development, of forming a dye having a suitable diffusibility, such as those described in British Pat. No. 2,083,640A. Other examples of usable couplers include colored couplers capable of exerting color correction effects, couplers capable of releasing development inhibitors during the course of development (so-called DIR couplers), as well as non-color-forming DIR coupling compounds capable of releasing development inhibitors and forming colorless coupling products.

In addition to these couplers, the photographic light-sensitive materials of the present invention may be incorporated with non-color-forming couplers capable of forming colorless coupling products, infrared couplers capable of forming dyes which absorb infrated rays upon the coupling reaction, black color-forming couplers capable of forming black dye images upon the coupling reaction, or the like.

Specific examples of magenta color-forming couplers usable in the present invention include those described in U.S. Pat. Nos. 2,600,788, 2,983,608, 3,062,653, 3,127,267, 3,311,476, 3,419,391, 3,519,429, 3,558,319, 3,582,322, 3,615,506, 3,834,908, 3,891,445, 3,926,631, 3,928,044, 4,076,533, 4,189,321 and 4,220,470, West German Pat. No. 1,810,464, West German Patent Application (OLS) Nos. 2,408,665, 2,417,945, 2,418,959, 2,424,467, 2,536,191, 2,651,363, 2,935,848 and 2,944,601, Japanese Patent Publication Nos. 6031/65, 38498/79, 10901/80, 29420/80 and 29421/80, and Japanese Patent Application (OPI) Nos. 74027/74, 129538/74, 60233/75, 159336/75, 20826/76, 26541/76, 36938/76, 105820/76, 42121/77, 58922/77, 9122/78, 55122/78, 48540/79, 80744/79, 62454/80 and 118034/80, etc.

Specific examples of yellow color-forming couplers which can be used in the present invention include those described in U.S. Pat. Nos. 2,875,057, 3,265,506, 3,408,194, 3,551,155, 3,582,322, 3,725,072, 3,891,445, 3,894,875, 3,973,968, 3,990,896, 4,008,086, 4,012,259, 4,022,620, 4,029,508, 4,046,575, 4,057,432, 4,059,447, 4,095,983, 4,133,958, 4,157,919, 4,182,630, 4,186,019, 4,203,768 and 4,206,278, West German Pat. No. 1,547,868, West German Patent Application (OLS) Nos. 2,213,461, 2,219,917, 2,261,361, 2,263,875, 2,414,006, 2,528,638, 2,935,849 and 2,936,842, British Pat. No. 1,425,020, Japanese Patent Publication Nos. 13576/74, 10783/76, 36856/79 and 13023/80, Japanese Patent Application (OPI) Nos. 26133/72, 66835/73, 6341/75, 34232/75, 87650/75, 130442/75, 75521/76, 102636/76, 145319/76, 21827/76, 82424/77, 115219/77, 48541/79, 121126/79, 2300/80, 36900/80, 38576/80 and 70841/80, and *Research Disclosure* No. 18053, etc.

Specific examples of cyan color-forming couplers which can be used in the present invention include those described in U.S. Pat. Nos. 2,369,929, 2,434,272, 2,474,293, 2,521,908, 2,895,826, 3,034,892, 3,311,476, 3,458,315, 3,476,563, 3,583,971, 3,591,383, 3,758,308, 3,767,411, 4,004,929, 4,052,212, 4,124,396, 4,146,396 and 4,205,990, West German Patent Application (OLS) Nos. 2,214,489, 2,414,830, 2,454,329, 2,634,694, 2,841,166, 2,934,769, 2,945,813, 2,947,707 and 3,005,355, Japanese Patent Publication Nos. 37822/79 and 37823/79, and Japanese Patent Application (OPI) Nos. 5055/73, 59838/73, 130441/75, 26034/76, 146828/76, 69824/77, 90932/77, 52423/78, 105226/78, 110530/78, 14736/79, 48237/79, 66129/79, 13193/79, 32071/80, 65957/80, 73050/80 and 108662/80, etc.

Specific examples of colored couplers usable in the present invention include those described in U.S. Pat. Nos. 2,521,908, 3,034,892 and 3,476,560, West German Patent Application (OLS) No. 2,418,959, Japanese Patent Publication Nos. 22335/63, 11340/67, 2016/69 and 32461/69, and Japanese Patent Application (OPI) Nos. 26034/76 and 42121/77, etc.

Specific examples of DIR couplers usable in the present invention include those described in U.S. Pat. Nos. 3,227,554, 3,617,291, 3,632,345, 3,701,783, 3,790,384, 3,933,500, 3,938,996, 4,052,213, 4,157,916, 4,171,223, 4,183,752, 4,187,110 and 4,226,934, West German Patent Application (OLS) Nos. 2,414,006, 2,454,301, 2,454,329, 2,540,959, 2,707,489, 2,709,688, 2,730,824, 2,754,281, 2,835,073, 2,853,362, 2,855,697 and 2,902,681, British Pat. No. 953,454, Japanese Patent Publication Nos. 16141/76, 2776/78 and 34933/80, Japanese Patent Application (OPI) Nos. 122335/74, 69624/77, 154631/77, 7232/78, 9116/78, 15136/78, 20324/78, 29717/78, 13533/78, 143223/78, 73033/79, 114241/79, 115229/79, 145135/79, 84935/80, 135835/80 and 151944/82, and *Research Disclosure*, No. 18104, etc. Other examples of usable development inhibitor releasing couplers include those which release development inhibitors with the action of a timing group, as described in U.S. Pat. No. 4,248,962, British Pat. No. 2,072,363, and Japanese Patent Application (OPI) Nos. 56837/82, 154234/82 and 188035/82, etc., and those which release DIR coupler components as described in Japanese Patent Application (OPI) No. 111536/82, etc.

The photographic light-sensitive materials of the present invention can be incorporated with compounds capable of releasing development inhibitors during the course of development, other than DIR couplers. Examples of such compounds usable include those described in U.S. Pat. Nos. 3,297,445 and 3,379,529, West German Patent Application (OLS) No. 2,417,914, and Japanese Patent Application (OPI) Nos. 15271/77 and 9116/78, etc.

Specific examples of non-color-forming couplers which can be used in the present invention include those described in U.S. Pat. Nos. 3,912,513 and 4,204,867, and Japanese Patent Application (OPI) No. 152721/77, etc.

Examples of usable infrared couplers include those described in U.S. Pat. No. 4,178,183, Japanese Patent Application (OPI) No. 129036/78 and Research Disclosure, Nos. 13460 and 18732, etc.

Specific examples of usable black color-forming couplers include those described in U.S. Pat. Nos. 4,126,461, 4,137,080 and 4,200,466, and Japanese Patent Application (OPI) Nos. 46029/78, 133432/78, 105247/80 and 105248/80, etc.

In addition to the above-described couplers, couplers which release coupling components as described in Japanese Patent Application Nos. 111536/82 and 111537/82, etc., and couplers which release groups capable of being subjected to an oxidation-reduction reaction with the oxidation products of color developing agents as described in Japanese Patent Application (OPI) No. 138636/82, etc., may be used for the purpose of improving photographic properties such as graininess, color reproducibility, etc.

The emulsion layers of the photographic light-sensitive materials of the present invention can be incorporated with a polymeric coupler, in combination with the coupler according to the invention. Specific examples of usable polymeric couplers include those described in U.S. Pat. Nos. 2,698,797, 2,759,816, 2,852,381, 3,163,652, 3,208,977, 3,311,552, 3,299,013, 3,370,952, 3,424,583, 3,451,820, 3,515,557, 3,767,412, 3,913,513, 3,926,436, 4,080,211, 4,128,427 and 4,215,195, Research Disclosure, Nos. 17825, 18815 and 19033, British Pat. No. 2,092,573A, and West German Patent Application (OLS) No. 3,217,200A, etc.

The couplers according to the present invention can be used in an amount of from $10^{-7}$ to 10% by mole, preferably from $10^{-6}$ to $10^{-1}$% by mole, based on the total amount of couplers used. The total amount of couplers used can be in the range of from $2\times10^{-3}$ to $5\times10^{-1}$, preferably from $1\times10^{-2}$ to $5\times10^{-1}$, per mole of silver.

The couplers according to the present invention can be incorporated into silver halide emulsion layers by known methods, including those described, e.g., in U.S. Pat. No. 2,322,027. For example, the couplers can be dissolved into a solvent and then dispersed into a hydrophilic colloid. Examples of solvents used for this process include organic solvents having a high boiling point, such as alkyl esters of phthalic acid (e.g., dibutyl phthalate, dioctyl phthalate, etc.), phosphates (e.g., diphenyl phosphate, triphenyl phosphate, tricresyl phosphate, dioctyl butyl phosphate, etc.), citrates (e.g., tributyl acetyl citrate, etc.), benzoates (e.g., octyl benzoate, etc.), alkylamides (e.g., diethyl laurylamides, etc.), esters of fatty acids (e.g., dibutoxyethyl succinate, dioctyl azelate, etc.) and trimesates (e.g., tributyl trimesate, etc.); and organic solvents having a boiling point of from about 30° to about 150° C., such as lower alkyl acetates (e.g., ethyl acetate, butyl acetate, etc.), ethyl propionate, secondary butyl alcohol, methyl isobutyl ketone, $\beta$-ethoxyethyl acetate, methyl cellosolve acetate, or the like. Mixtures of organic solvents having a high boiling point and organic solvents having a low boiling point can also be used.

It is also possible to utilize the dispersing method using polymers, as described in Japanese Patent Publication No. 39853/76 and Japanese Patent Application (OPI) No. 59943/76.

Of the couplers according to the present invention, those having an acidic group, such as a carboxy group or a sulfo group, can be introduced into hydrophilic colloids as an aqueous alkaline solution.

In the photographic light-sensitive materials of the present invention, any silver halide can be used in photographic emulsion layers thereof, including silver bromide, silver iodobromide, silver iodochlorobromide, silver chlorobromide and silver chloride. Silver iodobromide is preferable.

The photographic emulsions used in the light-sensitive materials of the present invention can be spectrally sensitized by methine dyes or the like. Such sensitizing dyes can be used either alone or in combination. Combinations of sensitizing dyes can be used for the purpose of supersensitization. The photographic emulsions can also contain a sensitizing dye in combination with a dye which per se exerts no sensitizing effect or in combination with a compound which exhibits no substantial absorptions in the visible region of the spectrum, to attain supersensitizing effect. Examples of useful sensitizing dyes and combinations of dyes for supersensitization are described, for example, in Research Disclosure, Vol. 176, No. 17643, IV-J, page 23 (December, 1978).

The hydrophilic colloid layers in the photographic light-sensitive materials of the present invention can be incorporated with water-soluble dyes as filter dyes or for the purpose of preventing irradiation or for other various purposes. Examples of such dyes include oxonol dyes, hemioxonol dyes, styryl dyes, merocyanine dyes, cyanine dyes and azo dyes. Of these dyes, oxonol dyes, hemioxonol dyes and merocyanine dyes can be particularly useful.

The photographic emulsion layers of the photographic light-sensitive materials of the present invention can be additionally incorporated with such compounds as polyalkylene oxides or derivatives thereof (e.g., ethers, esters, amines, etc.), thioether compounds, thiomorpholines, quaternary ammonium compounds, urethane derivatives, urea derivatives, imidazole derivatives and 3-pyrazolidones, in order to increase sensitivity and contrast, or to accelerate development thereof. Examples of such compounds usable include those described in U.S. Pat. Nos. 2,400,532, 2,423,549, 2,716,062, 3,617,280, 3,772,021 and 3,808,003, British Pat. No. 1,488,991, etc.

The photographic emulsions used in the present invention can be incorporated with various compounds for the purpose of stabilizing photographic properties or preventing fogs during production, storage or photographic processing thereof. Examples of usable antifoggants or stabilizers include azoles, such as benzothiazoliums, nitroindazoles, triazoles, benzotriazoles and benzimidazoles (in particular, nitro- or halogen-substituted benzimidazoles); heterocyclic mercapto compounds, such as mercaptothiazoles, mercaptobenzothiazoles, mercaptobenzimidazoles, mercaptothiadiazoles, mercaptotetrazoles (in particular, 1-phenyl-5-mercaptotetrazole) and mercaptopyrimidines; heterocyclic mercapto compounds as described above containing such water-solubilizing groups as carboxy and sulfo groups; thioketo compounds, such as oxazolinethiones; azaindene, such as tetraazaindenes (in particular, 4-hydroxy-substituted-(1,3,3a,7)tetraazaindenes); benzenethiosulfonic acids; benzenesulfinic acids; and the like.

In order to prevent color fogs, the photographic light-sensitive materials of the present invention can be incorporated with such compounds as hydroquinone derivatives, aminophenol derivatives, gallic acid derivatives and ascorbic acid derivatives, etc.

In the practice of the present invention, there can be additionally used known color fading preventing agents, including hydroquinone derivatives, gallic acid derivatives, p-alkoxyphenols, p-oxyphenol derivatives, bisphenols, and the like. Further, dye image stabilizers usable in the present invention can be used individually or a mixture of two or more thereof.

In the photographic light-sensitive material of the present invention the hydrophilic colloid layers may contain ultraviolet ray absorbing agents. Examples of usable ultraviolet ray absorbing agents include benzotriazole compounds substituted with an aryl group, 4-thiazolidone compounds, benzophenone compounds, cinnamic acid ester compounds, butadiene compounds, benzoxazole compounds, and ultraviolet ray absorbing polymers, etc. These ultraviolet ray absorbing agents may be fixed in the above-described hydrophilic colloid layers.

The present invention will be explained in greater detail with reference to the following examples, but the present invention should not be construed as being limited thereto.

EXAMPLE 1

In order to evaluate the effectivity of the compounds according to the present invention, samples were prepared by coating on a cellulose triacetate film support provided with a subbing layer a coating solution which was prepared by dissolving each of the compounds according to the present invention and the comparison compounds therefor as set forth in Table 1 below in a mixture of tricresyl phosphate and ethyl acetate together with Yellow Coupler C-1, emulsifying the solution into an aqueous gelatin solution and adding to a photographic emulsion. The amounts of each compounds coated are shown in $g/m^2$ or $mol/m^2$ in parentheses or in Table 1 below.

(1) Emulsion Layer

A silver iodobromide negative type emulsion (particle size: $0.7\mu$, silver coated amount: $8.2 \times 10^{-3} mol/m^2$).

Yellow Coupler C-1 ($8.2 \times 10^{-4} mol/m^2$).

Tricresyl phosphate ($0.4 g/m^2$).

Gelatin ($1.6 g/m^2$).

(2) Protective Layer

Gelatin ($1.30 g/m^2$).

H-1($0.05 g/m^2$).

These films were preserved under the condition of 40° C. and 40% RH for 28 days and also these films were preserved under refrigeration for 28 days. These films were subjected to sensitometric exposure with white light and then to the following development processing at a temperature of 38° C.

| | |
|---|---|
| 1. Color Development | 3 min 15 sec |
| 2. Bleaching | 6 min 30 sec |
| 3. Washing | 3 min 15 sec |
| 4. Fixing | 6 min 30 sec |
| 5. Washing | 3 min 15 sec |
| 6. Stabilizing | 3 min 15 sec |

The processing solutions used above had the following compositions:

| | |
|---|---|
| Color Developing Solution: | |
| Sodium nitrilotriacetate | 1.0 g |
| Sodium sulfite | 4.0 g |
| Sodium carbonate | 30.0 g |
| Potassium bromide | 1.4 g |
| Hydroxylamine sulfate | 2.4 g |
| 4-(N—ethyl-N—β-hydroxyethylamino)-2-methylaniline sulfate | 4.5 g |
| Water to make | 1 liter |
| Bleaching Solution: | |
| Ammonium bromide | 160.0 g |
| Aqueous ammonia (28%) | 25.0 ml |
| Sodium iron ethylenediaminetetraacetate | 130 g |
| Glacial acetic acid | 14 ml |
| Water to make | 1 liter |
| Fixing Solution: | |
| Sodium tetrapolyphosphate | 2.0 g |
| Sodium sulfite | 4.0 g |
| Ammonium thiosulfate (70%) | 175.0 ml |
| Sodium bisulfite | 4.6 g |
| Water to make | 1 liter |
| Stabilizing Solution: | |
| Formalin | 8.0 ml |
| Water to make | 1 liter |

The density of the thus processed samples was measured using blue light. The results obtained are shown in Table 1 below.

TABLE 1

| Sample | Coupler | Amount* Added | Preservation under Refrigeration | | | Preservation under 40° C. and 40% RH | | |
|---|---|---|---|---|---|---|---|---|
| | | | Fog | Gamma | Relative** Sensitivity | Fog | Gamma | Relative Sensitivity |
| 1 (Control) | — | — | 0.07 | 1.35 | 100 | 0.08 | 1.31 | 95 |
| 2 (Comparison) | C-2 | 30 | 0.08 | 1.67 | 124 | 0.14 | 1.56 | 100 |
| 3 (Comparison) | C-3 | 30 | 0.10 | 1.52 | 124 | 0.18 | 1.38 | 105 |
| 4 (Comparison) | C-4 | 1.5 | 0.21 | 1.58 | 120 | 0.27 | 1.32 | 100 |
| 5 (Present Invention) | (1) | 1.5 | 0.08 | 1.55 | 135 | 0.08 | 1.60 | 141 |
| 6 (Present Invention) | (15) | 0.1 | 0.10 | 1.53 | 124 | 0.11 | 1.53 | 124 |
| 7 (Present Invention) | (9) | 0.5 | 0.08 | 1.57 | 140 | 0.09 | 1.60 | 144 |

*Amount added: mol % to the amount of C-1
**Relative sensitivity: reciprocal of the exposure amount required for obtaining a color density of fog value + 0.2 and the sensitivity of Sample 1 preserved under refrigerator is taken as 100 and the other sensitivities are shown relatively.

The couplers and hardener used for preparing these samples are as follows:

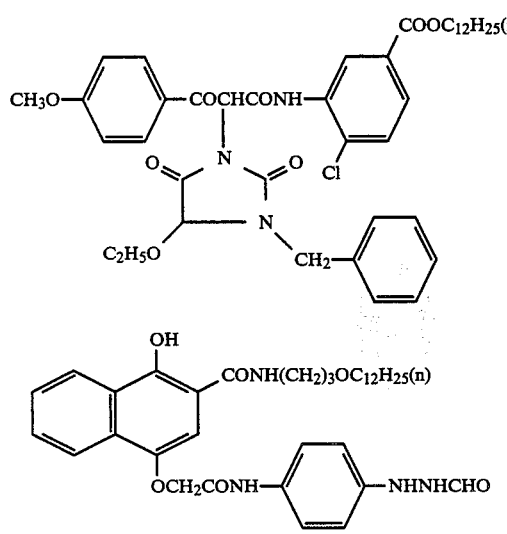

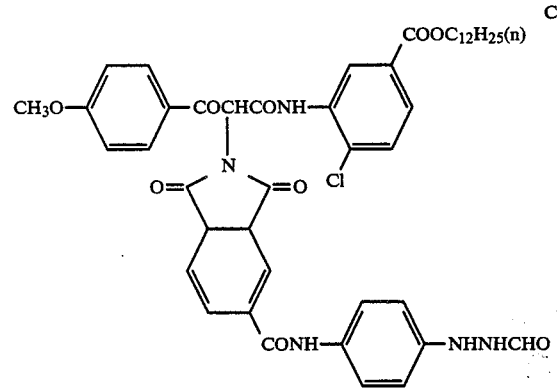

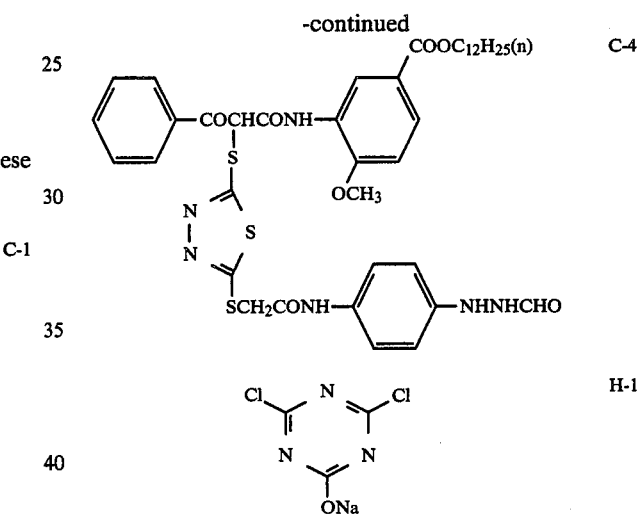

From the results shown in Table 1 above it is apparent that Samples 5 to 7 containing the compounds according to the present invention exhibit a little increase in fog and almost no decrease in sensitivity, although in Comparison Samples 2 to 4 the increase in fog and the decrease in sensitivity are remarkable. Accordingly, the compounds according to the present invention are clearly superior to the comparison couplers.

EXAMPLE 2

Sample 201

On a cellulose triacetate film support were coated layers having the compositions set forth below to prepare a multilayer color photographic light-sensitive material.

First Layer: Antihalation Layer

A gelatin layer containing black colloidal silver.

Second Layer: Intermediate Layer

A gelatin layer containing a dispersion of 2,5-di-tert-octylhydroquinone.

Third Layer: First Red-Sensitive Emulsion Layer

A silver iodobromide emulsion (iodide content: 5 mol%), silver coated amount: 1.9 g/m².

| | |
|---|---|
| Sensitizing Dye I | $6 \times 10^{-5}$ mol per mol of silver |
| Sensitizing Dye II | $1.5 \times 10^{-5}$ mol per mol of silver |
| Coupler C-5 | 0.04 mol per mol of silver |
| Coupler C-6 | 0.003 mol per mol of silver |
| Coupler C-7 | 0.0006 mol per mol of silver |

Fourth Layer: Second Red-Sensitive Emulsion Layer

A silver iodobromide emulsion (iodide content: 8 mol%), silver coated amount: 1.6 g/m².

| | |
|---|---|
| Sensitizing Dye I | $2.5 \times 10^{-5}$ mol per mol of silver |
| Sensitizing Dye II | $1.0 \times 10^{-5}$ mol per mol of silver |
| Coupler C-8 | 0.02 mol per mol of silver |
| Coupler C-6 | 0.0016 mol per mol of silver |

Fifth Layer: Intermediate Layer

Same as the Second Layer.

Sixth Layer: First Green-Sensitive Emulsion Layer

A silver iodobromide emulsion (iodide content: 4 mol%), silver coated amount: 1.6 g/m².

| | |
|---|---|
| Sensitizing Dye III | $3 \times 10^{-5}$ mol per mol of silver |
| Sensitizing Dye IV | $1 \times 10^{-5}$ mol per mol of silver |
| Coupler C-9 | 0.05 mol per mol of silver |
| Coupler C-10 | 0.008 mol per mol of silver |
| Coupler C-7 | 0.0015 mol per mol of silver |

Seventh Layer: Second Green-Sensitive Emulsion Layer

A silver iodobromide emulsion (iodide content: 8 mol%), silver coated amount: 1.8 g/m².

| | |
|---|---|
| Sensitizing Dye III | $2.5 \times 10^{-5}$ mol per mol of silver |
| Sensitizing Dye IV | $0.8 \times 10^{-5}$ mol per mol of silver |
| Coupler C-11 | 0.003 mol per mol of silver |
| Coupler C-12 | 0.017 mol per mol of silver |

Eighth Layer: Yellow Filter Layer

A gelatin layer containing yellow colloidal silver and a dispersion of 2,5-di-tert-octylhydroquinone.

Ninth Layer: First Blue-Sensitive Emulsion Layer

A silver iodobromide emulsion (iodide content: 6 mol), silver coated amount: 1.6 g/m².

| | |
|---|---|
| Coupler C-1 | 0.25 mol per mol of silver |
| Coupler C-7 | 0.015 mol per mol of silver |

Tenth Layer: Second Bleu-Sensitive Emulsion Layer

A silver iodobromide emulsion (iodide content: 8 mol%), silver coated amount: 1.1 g/m².

| | |
|---|---|
| Coupler C-1 | 0.06 mol per mol of silver |

Eleventh Layer: First Protective Layer

A gelatin layer containing silver iodobromide (iodide content: 1 ml%, average particle size: $0.07\mu$), silver coated amount: 0.5 g/m² and a dispersion of Ultraviolet Ray Absorbing Agent UV-1.

Twelfth Layer: Second Protective Layer

A gelatin layer containing polymethyl methacrylate particles (having a diameter of about $1.5\mu$).

A gelatin hardener and a surface active agent were incorporated into each of the layers in addition to the above-described components.

The sample thus prepared was designated Sample 201.

Samples 202 to 207

Samples 202 to 207 were prepared in the same manner as described in Sample 1 except that the compounds according to the present invention and the comparison compounds as shown in Table 2 below were further added in the amount set forth in Table 2 below in stead of Yellow Coupler C-1 in the Tenth Layer of Sample 201, respectively.

A series of Samples 202 to 207 was preserved under refrigeration for 7 days and another series of the samples was preserved under the condition of 40° C. and 80% RH for 7 days. These samples were subjected to sensitomeric exposure with white light and then to the same color development processing as described in Example 1. The density of the thus processed samples were measured using blue light. The photograhic properties obtained are shown in Table 2 below.

TABLE 2

| Sample | Coupler | Amount Added | Preservation under Refrigeration | | Preservation under High Temperature | |
|---|---|---|---|---|---|---|
| | | | Minimum Density | Relative Sensitivity | Minimum Density | Relative Sensitivity |
| 201 (Control) | — | — | 0.51 | 100 | 0.51 | 98 |
| 202 (Comparison) | C-2 | 30 | 0.52 | 105 | 0.54 | 103 |
| 203 (Comparison) | C-3 | 30 | 0.54 | 115 | 0.59 | 100 |
| 204 (Comparison) | C-4 | 1.5 | 0.53 | 120 | 0.61 | 95 |
| 205 (Present Invention) | (1) | 1.5 | 0.51 | 120 | 0.51 | 118 |
| 206 (Present Invention) | (15) | 0.3 | 0.53 | 115 | 0.54 | 112 |
| 207 (Present Invention) | (9) | 1.0 | 0.52 | 118 | 0.53 | 120 |

From the results shown in Table 2 above it is apparent that Sample 205 to 207 containing the compounds according to the present invention exhibit almost no increase in fog and maintain high sensitivity, although in Comparison Samples 202 to 204 the increase in fog and the decrease in sensitivity are observed upon the preservation under the high temperature condition.

The compounds used for preparing the sample are as follows:

Sensitizing Dye I: Pyridinium salt of anhydro-5,5'-dichloro-3,3'-di(γ-sulfopropyl)-9-ethylthiacarbocyanine hydroxide Sensitizing Dye II: Triethylamine salt of anhydro-9-ethyl-3,3'-di(γ-sulfopropyl)-4,5,4',5'-dibenzothiacarbocyanine hydroxide Sensitizing Dye III: Sodium salt of anhydro-9-ethyl-5,5'-dichloro-3,3'-di(γ-sulfopropyl)oxacarbocyanine Sensitizing Dye IV: Sodium salt of anhydro-5,6,5',6'-tetrachloro-1,1'-diethyl-3,3'-di{β-[β-(γ-sulfopropoxy)ethoxy]ethyl}imidazolocarbocyanine hydroxide

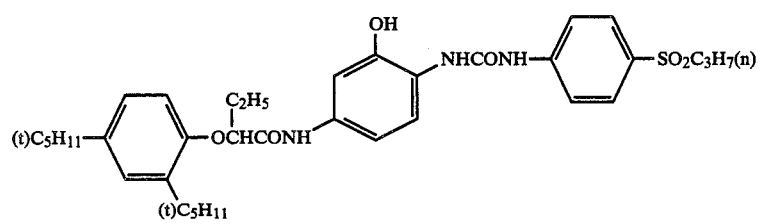

C-5

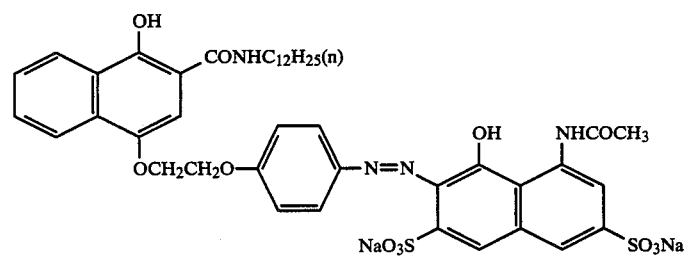

C-6

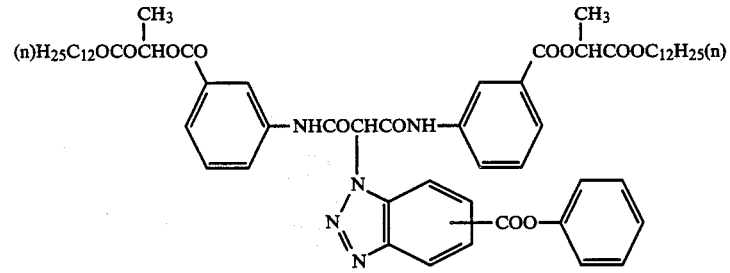

C-7

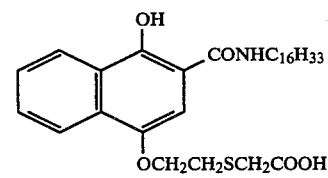

C-8

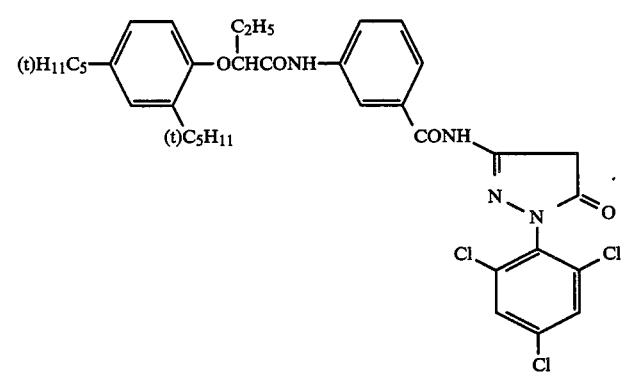

C-9

C-10
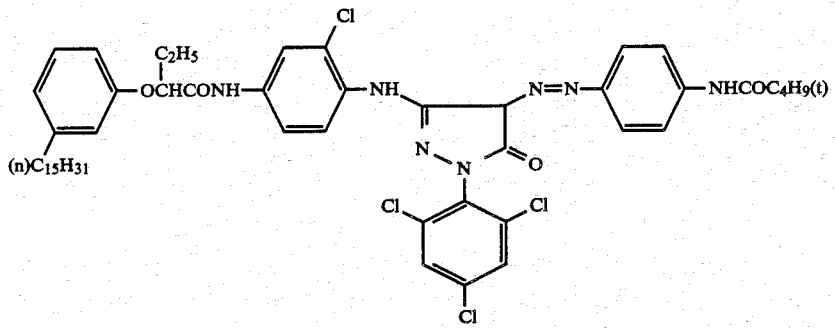

C-11
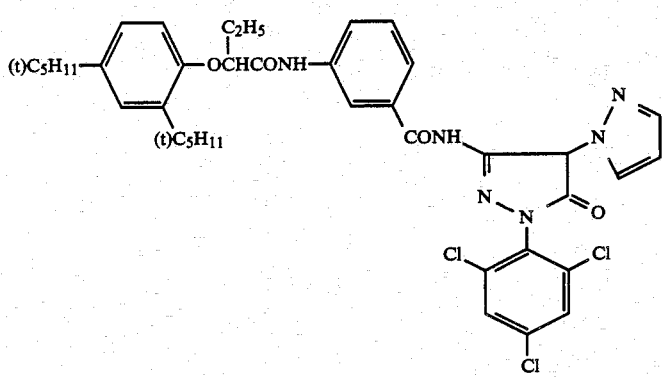

C-12
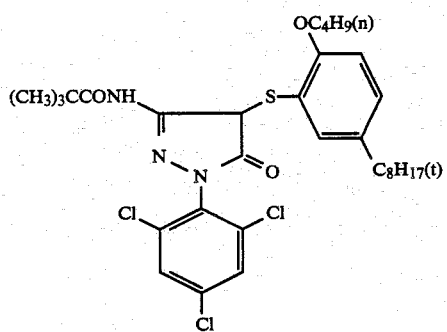

While the invention has been described in detail and with reference to specific embodiments thereof, it will be apparent to one skilled in the art that various changes and modifications can be made therein without departing from the spirit and scope thereof.

What is claimed is:

1. A silver halide color photographic light-sensitive material comprising a support having thereon a silver halide emulsion layer and a compound represented by the following general formula (I):

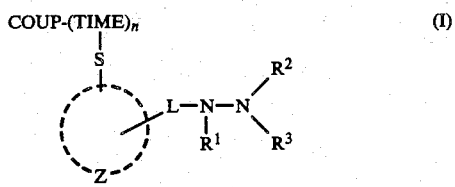

wherein COUP represents a coupler residue capable of being subjected to a coupling reaction with an oxidation product of an aromatic primary amine developing agent; TIME represents a timing group which is released upon the coupling reaction and subsequently releases

Z represents a 5- or 6-membered monocyclic heterocyclic ring or a 9-membered condensed heterocyclic ring, said heterocyclic ring consisting of nitrogen and carbon atoms; L represents a divalent linking group selected from the groups having the following formulae:

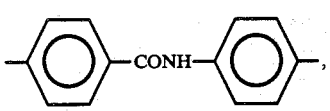

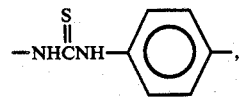

-continued

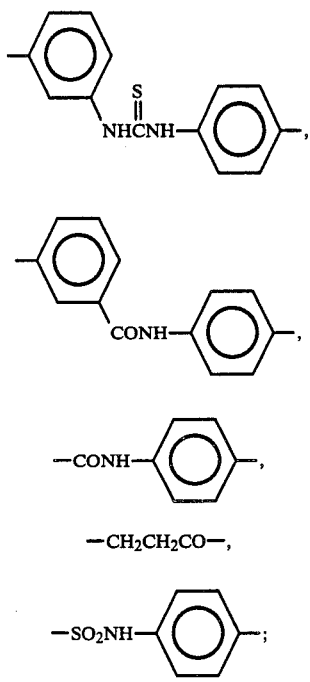

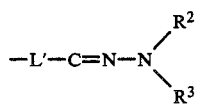

$R^1$ represents a hydrogen atom or an alkoxycarbonyl group; $R^2$ represents a hydrogen atom, an alkyl group, an aryl group, a heterocyclic group, an acyl group, a sulfonyl group, an alkoxycarbonyl group, a carbamoyl group, a sulfamoyl group, a thioacyl group or a thiocarbamoyl group; $R^3$ represents a hydrogen atom; $R^2$ and $R^3$ may be bonded to each other to form a hydrazone structure; a part of L and $R^1$ may be bonded to each other to form a hydrazone structure; and n represents 0 or 1.

2. A silver halide color photographic light-sensitive material as claimed in claim 1, wherein the hydrazone structure formed with a part of L and $R^1$ is a group of the formula $$-L'-C=N-N\begin{matrix}R^2\\R^3\end{matrix}$$

wherein $R^2$ and $R^3$ are defined in claim 1 and $R^4$ represents a hydrogen atom, an alkyl group or an aryl group and L' represents a divalent linking group having the formula $-CH_2CH_2-$.

3. A silver halide color photographic light-sensitive material as claimed in claim 1, wherein the coupler residue is a residue of a cyan color-forming coupler selected from the group consisting of phenol couplers and naphthol couplers.

4. A silver halide color photographic light-sensitive material as claimed in claim 1, wherein the coupler residue is a residue of a magenta color-forming coupler selected from the group consisting of 5-pyrazolone couplers, pyrazolobenzimidazole couplers, pyrazolotriazole couplers, cyanoacetylcoumarone couplers, open chain acylacetonitrile couplers and indazolone couplers.

5. A silver halide color photographic light-sensitive material as claimed in claim 1, wherein the coupler residue is a residue of a yellow color-forming coupler selected from the group consisting of benzoylacetanilide couplers, pivaloylacetanilide couplers and malondianilide couplers.

6. A silver halide color photographic light-sensitive material as claimed in claim 1, wherein the coupler residue is a residue of a non-color-forming coupler selected from the group consisting of indanones, cyclopentanones, diesters of malonic acid, imidazolinones, oxazolinones and thiazolinones.

7. A silver halide color photographic light-sensitive material as claimed in claim 1, wherein the coupler residue is a residue represented by the following general formula (II), (III), (IV), (V), (VI), (VII), (VIII), (IX) or (X):

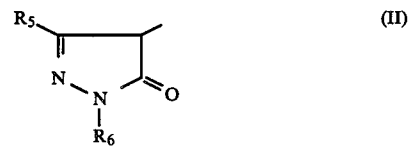

wherein $R_5$ represents an acylamido group, an anilino group or a ureido group; and $R_6$ represents a phenyl group which may be substituted with one or more substituents selected from a halogen atom, an alkyl group, an alkoxy group or a cyano group,

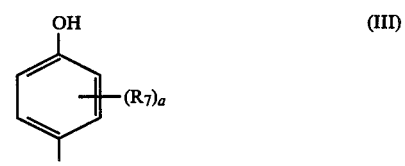

wherein $R_7$ represents a halogen atom, an acylamido group, or an aliphatic group; and a represents an integer of 1 to 4,

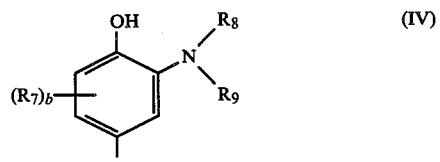

wherein $R_7$ has the same meaning as defined above; $R_8$ and $R_9$ each represents an aliphatic group, an aromatic group, a carbamoyl group or a heterocyclic group, either of $R_8$ and $R_9$ may be a hydrogen atom; and b represents 0 or an integer of 1 to 3,

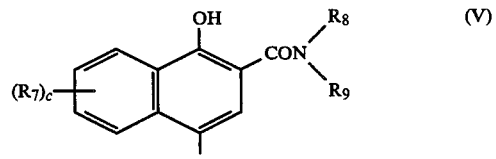

wherein R₇, R₈ and R₉ each has the same meaning as defined above; and c represents 0 or an integer of 1 to 5,

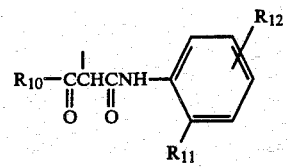 (VI)

wherein R₁₀ represents a tertiary alkyl group or an aromatic group; R₁₁ represents a hydrogen atom, a halogen atom or an alkoxy group; and R₁₂ represents an acylamido group, an aliphatic group, an alkoxycarbonyl group, a sulfamoyl group, a carbamoyl group, an alkoxy group, a halogen atom or a sulfonamido gorup,

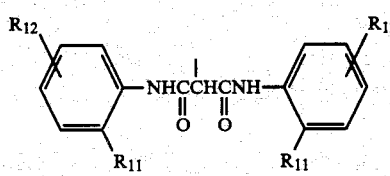 (VII)

wherein R₁₁ and R₁₂ each has the same meaning as defined above,

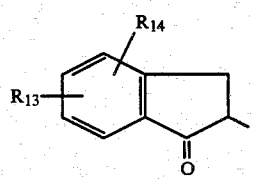 (VIII)

wherein R₁₃ represents an aliphatic group, an alkoxy group, a mercapto group, an alkylthio group, an acylamido group, an alkoxycarbonyl group, a sulfonamido group, a carbamoyl group, a sulfamoyl group, an alkoxysulfonyl group, an aryloxysulfonyl group, an acyl group, a diacylamino group, an alkylsulfonyl group or an arylsulfonyl group; and R₁₄ represents a hydrogen atom, a halogen atom, an alkoxy group, an acyl group, a nitro group, an alkylsulfonyl group or an arylsulfonyl group; or the group represented by general formula (VIII) above may be in the form of an enol ester thereof,

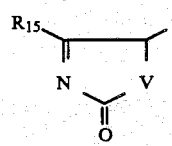 (IX)

wherein R₁₅ represents an aliphatic group or an aromatic group; and V represents an oxygen atom, a sulfur atom or a nitrogen atom,

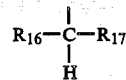 (X)

wherein R₁₆ and R₁₇ each represents a group selected from

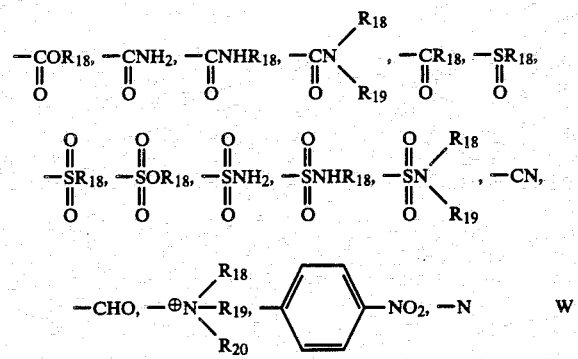

wherein R₁₈, R₁₉ and R₂₀ each represents a hydrogen atom, an aliphatic group, an aromatic group or a heterocyclic group; and W represents a non-metallic atomic group necessary to form a 5-membered or 6-membered ring together with the nitrogen atom; or R₁₆ and R₁₇ in combination may form a 5-membered or 6-membered ring together with a non-metallic atomic group necessary.

8. A silver halide color photographic light-sensitive material as claimed in claim 1, wherein the timing group is selected from a group which is released from COUP upon the coupling reaction and subsequently releases the group of

upon an intramolecular displacement reaction, a group which releases the group of

upon an electron transfer reaction via a conjugated system, and a group of coupling component capable of releasing the group of

upon the coupling reaction with the oxidation product of an aromatic primary amine developing agent.

9. A silver halide color photographic light-sensitive material as claimed in claim 1, wherein the heterocyclic ring represented by Z is a 5-membered or 6-membered ring.

10. A silver halide color photographic light-sensitive material as claimed in claim 1, wherein the heterocyclic ring represented by Z is selected from pyrrole, imidazole, pyrazole, triazole, tetrazole, benzimidazole, benzopyrazole, indole, imidazoline, pyrazoline, pyridine, pyrimidine, pyrazine, pyridazine, triazine, imidazotetrazole, pyrazolotriazole, tetraazaindene and pentaazaindene.

11. A silver halide color photographic light-sensitive material as claimed in claim 1, wherein an amount of the compound of the general formula (I) is from $10^{-7}$ to 10% by mole of the total amount of couplers present in the material.

12. A silver halide color photographic light-sensitive material as claimed in claim 11, wherein an amount of the compound of the general formula (I) is from $10^{-6}$ to $10^{-1}$% by mole of the total amount of couplers present in the material.

13. A silver halide color photographic light-sensitive material as claimed in claim 1, wherein the silver halide emulsion layer contains the compound of the general formula (I).

14. A silver halide color photographic light-sensitive material as claimed in claim 13, wherein the silver halide emulsion layer further contains a color forming coupler.

15. A multilayer color photographic light-sensitive material comprising a support having thereon at least one blue-sensitive silver halide emulsion layer containing a yellow color forming coupler, at least one green-sensitive silver halide emulsion layer containing a magenta color forming coupler and at least one red-sensitive silver halide emulsion layer containing a cyan color forming coupler wherein at least one of the silver halide emulsion layers contains a compound represented by the following general formula (I):

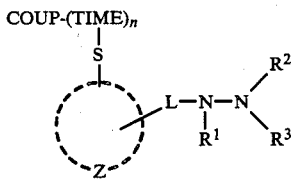

wherein COUP represents a coupler residue capable of being subjected to a coupling reaction with an oxidation product of an aromatic primary amine developing agent; TIME represents a timing group which is released upon the coupling reaction and subsequently releases

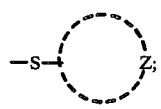

Z represents a 5- or 6-membered monocyclic heterocyclic ring or a 9-membered condensed heterocyclic ring, said ring consisting of nitrogen and carbon atoms; L represents a divalent linking group selected from the groups having the following formulae:

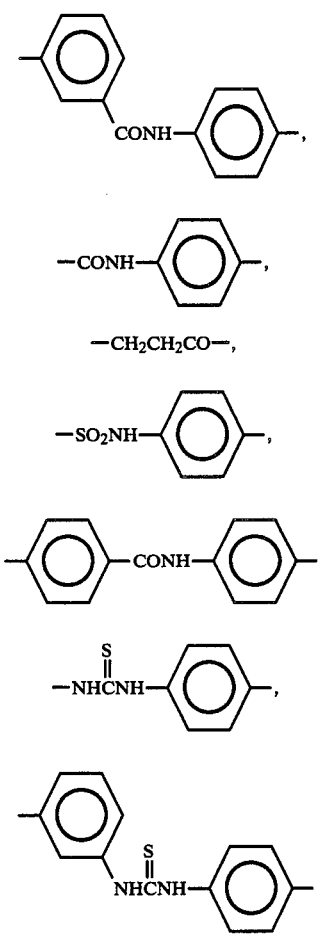

$R^1$ represents a hydrogen atom or an alkoxycarbonyl group; $R^2$ represents a hydrogen atom, an alkyl group, an aryl group, a heterocyclic group, an acyl group, a sulfonyl group, an alkoxycarbonyl group, a carbamoyl group, a sulfamoyl group, a thioacyl group or a thiocarbamoyl group; $R^3$ represents a hydrogen atom; $R^2$ and $R^3$ may be bonded to each other form a hydrazone structure; a part of L and $R^1$ may be bonded to each other to form a hydrazone structure; and n represents 0 or 1.

16. A method of forming an image of enhanced stability in a silver halide color photographic light-sensitive material comprising a support having thereon a silver halide emulsion layer comprising imagewise exposing and developing said photographic material, wherein said photographic material contains a compound represented by the following general formula (I):

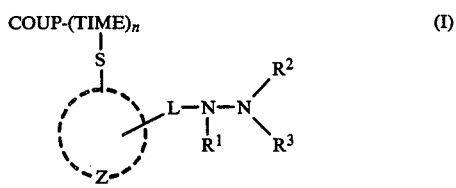

wherein COUP represents a coupler residue capable of being subjected to a coupling reaction with an oxidation product of an aromatic primary amine developing agent; TIME represents a timing group which is released upon the coupling reaction and subsequently releases

Z represents a 5- or 6-membered monocyclic heterocyclic ring or a 9-membered condensed heterocyclic ring, said heterocyclic ring consisting of nitrogen and carbon atoms; L represents a divalent linking group selected from the groups having the following formulae:

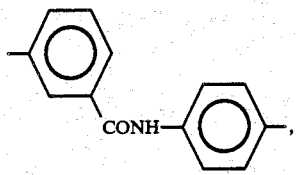

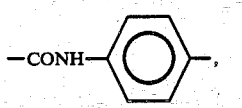

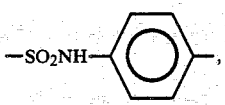

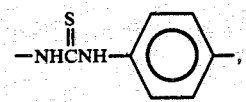

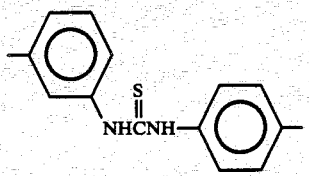

$R^1$ represents a hydrogen atom or an alkoxycarbonyl group; $R^2$ represents a hydrogen atom, an alkyl group, an aryl group, a heterocyclic group, an acyl group, a sulfonyl group, an alkoxycarbonyl group, a carbamoyl group, a sulfamoyl group, a thioacyl group or a thiocarbamoyl group; $R^3$ represents a hydrogen atom; $R^2$ and $R^3$ may be bonded to each other to form a hydrazone structure; a part of L and $R^1$ may be bonded to each other to form a hydrazone structure; and n represents 0 or 1.

17. A silver halide color photographic light-sensitive material as claimed in claim 11, wherein the total amount of couplers used are in the range of from $2\times 10^{-3}$ to $5\times 10^{-1}$ per mol of silver.

18. A silver halide color photographic light-sensitive material as claimed in claim 17, wherein the total amount of couplers used is in the range of from $1\times 10^{-2}$ to $5\times 10^{-1}$ per mol of silver.

19. A silver halide color photographic light-sensitive material as claimed in claim 1, said silver halide color photographic light-sensitive material having improved stability during storage.

* * * * *